(12) United States Patent
Olson

(10) Patent No.: US 12,082,936 B2
(45) Date of Patent: Sep. 10, 2024

(54) UNIFORM MAPPING BALLOON

(71) Applicant: St. Jude Medical, Cardiology Division, Inc., St. Paul, MN (US)

(72) Inventor: Gregory K. Olson, Elk River, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 664 days.

(21) Appl. No.: 17/256,997

(22) PCT Filed: Sep. 26, 2019

(86) PCT No.: PCT/IB2019/058192
§ 371 (c)(1),
(2) Date: Dec. 29, 2020

(87) PCT Pub. No.: WO2020/065587
PCT Pub. Date: Apr. 2, 2020

(65) Prior Publication Data
US 2021/0361220 A1    Nov. 25, 2021

Related U.S. Application Data

(60) Provisional application No. 62/737,395, filed on Sep. 27, 2018.

(51) Int. Cl.
*A61B 5/00* (2006.01)
*A61B 5/287* (2021.01)
(Continued)

(52) U.S. Cl.
CPC .............. *A61B 5/367* (2021.01); *A61B 5/287* (2021.01); *A61B 5/339* (2021.01); *A61B 5/6853* (2013.01); *A61B 2562/04* (2013.01)

(58) Field of Classification Search
CPC .................................................. A61B 55/367
See application file for complete search history.

(56) References Cited

U.S. PATENT DOCUMENTS

| | | | |
|---|---|---|---|
| 5,224,939 A | 7/1993 | Holman et al. | |
| 5,380,301 A | 1/1995 | Prichard et al. | |

(Continued)

FOREIGN PATENT DOCUMENTS

| | | |
|---|---|---|
| CN | 101927053 B | 1/2015 |
| CN | 103157168 B | 4/2015 |

(Continued)

*Primary Examiner* — John R Downey
*Assistant Examiner* — Anant A Gupta
(74) *Attorney, Agent, or Firm* — Kilpatrick Townsend & Stockton LLP

(57) ABSTRACT

A catheter including a catheter shaft and a mapping balloon configured for navigation within a body. The mapping balloon can be coupled to the catheter shaft, such as at a distal end of the catheter shaft. The mapping balloon can have an exterior surface including a plurality of predefined fold locations configured to allow the mapping balloon to be adjusted between a collapsed configuration and an expanded configuration. In the collapsed configuration, the mapping balloon can include a first dimension, and in the expanded configuration the mapping balloon can have a second dimension. The second dimension can be greater than the first dimension. A plurality of electrodes can be located along the exterior surface of the mapping balloon to communicate electrical signals with an electronic control unit.

20 Claims, 5 Drawing Sheets

(51) Int. Cl.
  *A61B 5/339*  (2021.01)
  *A61B 5/367*  (2021.01)

(56) References Cited

U.S. PATENT DOCUMENTS

| | | |
|---|---|---|
| 5,400,783 A | 3/1995 | Pomeranz et al. |
| 5,456,254 A | 10/1995 | Pietroski et al. |
| 5,593,405 A * | 1/1997 | Osypka .................. A61L 29/02 |
| | | 606/7 |
| 5,626,136 A | 5/1997 | Webster, Jr. |
| 5,715,817 A | 2/1998 | Stevens-Wright et al. |
| 5,715,832 A | 2/1998 | Koblish et al. |
| 5,827,278 A | 10/1998 | Webster, Jr. |
| 5,871,483 A | 2/1999 | Jackson et al. |
| 5,876,373 A | 3/1999 | Giba et al. |
| 6,074,379 A | 6/2000 | Prichard |
| 6,273,404 B1 | 8/2001 | Holman et al. |
| 6,491,681 B1 | 12/2002 | Kunis et al. |
| 6,554,794 B1 | 4/2003 | Mueller et al. |
| 7,004,937 B2 | 2/2006 | Lentz et al. |
| 7,214,220 B2 | 5/2007 | McGlinch et al. |
| 7,217,256 B2 | 5/2007 | Di Palma |
| 7,263,397 B2 | 8/2007 | Hauck et al. |
| 7,386,339 B2 | 6/2008 | Strommer et al. |
| 7,608,063 B2 | 10/2009 | Le et al. |
| 7,625,365 B2 | 12/2009 | McGlinch et al. |
| 7,666,204 B2 | 2/2010 | Thornton et al. |
| 7,959,601 B2 | 6/2011 | McDaniel et al. |
| 7,985,215 B2 | 7/2011 | Guo et al. |
| 8,103,327 B2 | 1/2012 | Harlev et al. |
| 8,137,321 B2 | 3/2012 | Argentine |
| 8,221,390 B2 | 7/2012 | Pal et al. |
| 8,273,016 B2 | 9/2012 | O'Sullivan |
| 8,376,990 B2 | 2/2013 | Ponzi et al. |
| 8,447,377 B2 | 5/2013 | Harlev et al. |
| 8,608,703 B2 | 12/2013 | Riles et al. |
| 8,649,880 B1 | 2/2014 | Parker, Jr. |
| 8,700,120 B2 | 4/2014 | Koblish |
| 8,706,193 B2 | 4/2014 | Govari et al. |
| 8,755,861 B2 | 6/2014 | Harlev et al. |
| 8,777,929 B2 | 7/2014 | Schneider et al. |
| 8,792,962 B2 | 7/2014 | Esguerra et al. |
| 8,814,824 B2 | 8/2014 | Kauphusman et al. |
| 8,814,825 B2 | 8/2014 | Tegg et al. |
| 8,882,705 B2 | 11/2014 | McDaniel et al. |
| 8,894,610 B2 | 11/2014 | Macnamara et al. |
| 8,996,091 B2 | 3/2015 | de la Rama et al. |
| 9,017,308 B2 | 4/2015 | Klisch et al. |
| 9,033,917 B2 | 5/2015 | Magana et al. |
| 9,050,010 B2 | 6/2015 | Bui et al. |
| 9,101,733 B2 | 8/2015 | McDaniel |
| 9,204,929 B2 | 12/2015 | Solis |
| 9,216,056 B2 | 12/2015 | Datta et al. |
| 9,247,990 B2 | 2/2016 | Kauphusman et al. |
| 9,326,815 B2 | 5/2016 | Watson |
| 9,339,631 B2 | 5/2016 | Graham et al. |
| 9,433,751 B2 | 9/2016 | Ponzi et al. |
| 9,433,752 B2 | 9/2016 | Jimenez et al. |
| 9,468,495 B2 | 10/2016 | Kunis et al. |
| 9,486,280 B2 | 11/2016 | Koblish et al. |
| 9,486,282 B2 | 11/2016 | Solis |
| 9,539,413 B2 | 1/2017 | Ogle |
| 9,649,158 B2 | 5/2017 | Datta et al. |
| 9,687,166 B2 | 6/2017 | Subramaniam et al. |
| 9,693,733 B2 | 7/2017 | Altmann et al. |
| 9,693,820 B2 | 7/2017 | Potter et al. |
| 9,694,159 B2 | 7/2017 | Schneider et al. |
| 9,694,161 B2 | 7/2017 | Selkee |
| 9,788,895 B2 | 10/2017 | Solis |
| 9,820,664 B2 | 11/2017 | Hoitink et al. |
| 9,844,645 B2 | 12/2017 | Pai et al. |
| 9,848,795 B2 | 12/2017 | Marecki et al. |
| 9,919,132 B2 | 3/2018 | Tegg et al. |
| 9,949,656 B2 | 4/2018 | Wu et al. |
| 9,986,949 B2 | 6/2018 | Govari et al. |
| 10,004,877 B2 | 6/2018 | Tegg |
| 10,034,637 B2 | 7/2018 | Harlev et al. |
| 10,052,457 B2 | 8/2018 | Nguyen et al. |
| 10,065,019 B2 | 9/2018 | Hamuro et al. |
| 10,099,036 B2 | 10/2018 | Heideman et al. |
| 10,118,022 B2 | 11/2018 | Helgeson et al. |
| 10,143,394 B2 | 12/2018 | Solis |
| 10,322,261 B2 | 6/2019 | Pai et al. |
| 10,362,952 B2 | 7/2019 | Basu et al. |
| 10,362,954 B2 | 7/2019 | de la Rama et al. |
| 10,376,170 B2 | 8/2019 | Quinn et al. |
| 10,384,036 B2 | 8/2019 | Romoscanu |
| 10,398,500 B2 | 9/2019 | Huszar et al. |
| 10,478,325 B2 | 11/2019 | Syed |
| 10,506,938 B2 | 12/2019 | Wu et al. |
| 10,537,259 B2 | 1/2020 | Wu et al. |
| 10,542,899 B2 | 1/2020 | Wu et al. |
| 10,556,091 B2 | 2/2020 | Truhler et al. |
| 10,575,742 B2 | 3/2020 | Wu et al. |
| 10,575,745 B2 | 3/2020 | Solis |
| 10,595,738 B2 | 3/2020 | Sterrett et al. |
| 10,595,740 B2 | 3/2020 | Hoitink et al. |
| 10,602,948 B2 | 3/2020 | Wu et al. |
| 10,646,692 B2 | 5/2020 | Tegg et al. |
| 10,653,423 B2 | 5/2020 | Starnes |
| 10,702,677 B2 | 7/2020 | Okamura et al. |
| 10,737,060 B2 | 8/2020 | Gupta et al. |
| 10,835,712 B2 | 11/2020 | Wada |
| 10,842,990 B2 | 11/2020 | de la Rama et al. |
| 10,857,349 B2 | 12/2020 | de la Rama et al. |
| 10,869,992 B2 | 12/2020 | Pai et al. |
| 10,898,685 B2 | 1/2021 | Tegg |
| 10,912,925 B2 | 2/2021 | Houck |
| 10,945,626 B2 | 3/2021 | Fuentes-Ortega et al. |
| 10,946,167 B2 | 3/2021 | Mintz et al. |
| 10,953,196 B2 | 3/2021 | Raab et al. |
| 10,959,636 B2 | 3/2021 | Dahlen et al. |
| 10,966,623 B2 | 4/2021 | Wu et al. |
| 10,966,753 B2 | 4/2021 | Coyle et al. |
| 10,967,150 B2 | 4/2021 | Helgeson et al. |
| 10,987,045 B2 | 4/2021 | Basu et al. |
| 11,033,715 B2 | 6/2021 | Beeckler et al. |
| 11,039,772 B2 | 6/2021 | Wu et al. |
| 11,039,773 B2 | 6/2021 | Sterrett et al. |
| 11,083,400 B2 | 8/2021 | Hoitink et al. |
| 11,116,436 B2 | 9/2021 | Wu et al. |
| 11,116,476 B2 | 9/2021 | Buesseler et al. |
| 11,123,051 B2 | 9/2021 | Van Der Linde et al. |
| 11,141,568 B2 | 10/2021 | Hsueh et al. |
| 11,160,482 B2 | 11/2021 | Solis |
| 11,172,858 B2 | 11/2021 | Olson et al. |
| 11,272,886 B2 | 3/2022 | Harlev et al. |
| 2002/0165484 A1 | 11/2002 | Bowe et al. |
| 2003/0088178 A1 * | 5/2003 | Owens .................. A61B 90/36 |
| | | 600/420 |
| 2009/0299355 A1 * | 12/2009 | Bencini .................. A61B 18/02 |
| | | 606/21 |
| 2014/0100639 A1 | 4/2014 | Lee et al. |
| 2015/0025533 A1 | 1/2015 | Groff et al. |
| 2015/0119911 A1 | 4/2015 | Mckenzie |
| 2015/0141982 A1 * | 5/2015 | Lee ........................ A61B 5/287 |
| | | 606/41 |
| 2016/0213423 A1 | 7/2016 | Kauphusman et al. |
| 2016/0278851 A1 | 9/2016 | Mannion et al. |
| 2016/0331933 A1 | 11/2016 | Knutsen |
| 2017/0319269 A1 | 11/2017 | Oliverius et al. |
| 2017/0367756 A1 | 12/2017 | Sliwa et al. |
| 2018/0042667 A1 | 2/2018 | Pappone et al. |
| 2018/0085064 A1 | 3/2018 | Auerbach et al. |
| 2018/0161093 A1 | 6/2018 | Basu et al. |
| 2018/0229030 A1 | 8/2018 | Dubuclet et al. |
| 2018/0369574 A1 | 12/2018 | Dubuclet et al. |
| 2019/0009052 A1 | 1/2019 | Oliverius et al. |
| 2019/0125378 A1 | 5/2019 | Shelton, IV et al. |
| 2019/0192826 A1 | 6/2019 | Wada |
| 2020/0077908 A1 | 3/2020 | Hagfors et al. |
| 2020/0121894 A1 | 4/2020 | Prabhu et al. |
| 2020/0138378 A1 | 5/2020 | de la Rama et al. |
| 2020/0214635 A1 | 7/2020 | Dahlen et al. |

(56) References Cited

U.S. PATENT DOCUMENTS

| | | | |
|---|---|---|---|
| 2020/0253496 A1 | 8/2020 | Deno et al. |
| 2020/0405166 A1 | 12/2020 | Wu et al. |
| 2021/0038860 A1 | 2/2021 | Mintz et al. |
| 2021/0145342 A1 | 5/2021 | Wang |
| 2021/0153932 A1 | 5/2021 | Voth et al. |
| 2021/0187246 A1 | 6/2021 | Houck |
| 2021/0204871 A1 | 7/2021 | Goedeke et al. |
| 2021/0268234 A1 | 9/2021 | Helgeson et al. |
| 2021/0298656 A1 | 9/2021 | Wu et al. |
| 2021/0361216 A1 | 11/2021 | Hoitink et al. |
| 2021/0401345 A1 | 12/2021 | Wu et al. |
| 2022/0023594 A1 | 1/2022 | Pai |
| 2022/0054066 A1 | 2/2022 | Solis |
| 2022/0061727 A1 | 3/2022 | Olson et al. |

FOREIGN PATENT DOCUMENTS

| | | |
|---|---|---|
| CN | 106859765 A | 6/2017 |
| CN | 206880930 U | 1/2018 |
| CN | 104958824 B | 12/2018 |
| CN | 104434083 B | 4/2019 |
| CN | 104968261 B | 5/2019 |
| CN | 105592778 B | 7/2019 |
| CN | 110536646 A | 12/2019 |
| CN | 110604860 A | 12/2019 |
| CN | 111225627 A | 6/2020 |
| CN | 111432739 A | 7/2020 |
| CN | 111657866 A | 9/2020 |
| CN | 106264715 B | 11/2020 |
| CN | 106264716 B | 11/2020 |
| CN | 112040861 A | 12/2020 |
| CN | 106308790 B | 6/2021 |
| CN | 107529958 B | 7/2021 |
| CN | 109310469 B | 7/2021 |
| CN | 109641121 B | 9/2021 |
| CN | 109952123 B | 9/2021 |
| CN | 110545874 B | 9/2021 |
| CN | 110559544 B | 9/2021 |
| CN | 113425304 A | 9/2021 |
| CN | 105615994 B | 10/2021 |
| CN | 109963610 B | 11/2021 |
| CN | 108289709 B | 3/2022 |
| EP | 0889744 B1 | 1/2004 |
| EP | 1254641 B1 | 11/2008 |
| EP | 1690564 B1 | 4/2009 |
| EP | 1723981 B1 | 8/2010 |
| EP | 2135634 B1 | 10/2011 |
| EP | 2018203 B1 | 6/2012 |
| EP | 1814450 B1 | 1/2013 |
| EP | 2269532 B1 | 3/2013 |
| EP | 2604306 B1 | 1/2014 |
| EP | 2875790 A2 | 5/2015 |
| EP | 2915555 A1 | 9/2015 |
| EP | 1968679 B1 | 9/2016 |
| EP | 2241279 B1 | 9/2016 |
| EP | 3115076 A4 | 10/2017 |
| EP | 3117863 A4 | 10/2017 |
| EP | 3111871 B1 | 3/2018 |
| EP | 3111872 B1 | 4/2018 |
| EP | 3057488 B1 | 5/2018 |
| EP | 2848226 B1 | 7/2018 |
| EP | 3363397 A1 | 8/2018 |
| EP | 3391928 A1 | 10/2018 |
| EP | 3122276 B1 | 11/2018 |
| EP | 3398549 A1 | 11/2018 |
| EP | 1759668 B1 | 12/2018 |
| EP | 3037122 B1 | 12/2018 |
| EP | 2234537 B1 | 1/2019 |
| EP | 2569040 B1 | 2/2019 |
| EP | 3023052 B1 | 3/2019 |
| EP | 3466363 A1 | 4/2019 |
| EP | 2550989 B1 | 6/2019 |
| EP | 3512589 A1 | 7/2019 |
| EP | 3512590 A1 | 7/2019 |
| EP | 3527125 A1 | 8/2019 |
| EP | 3531903 A1 | 9/2019 |
| EP | 3581229 A1 | 12/2019 |
| EP | 3434218 B1 | 2/2020 |
| EP | 2908723 B1 | 3/2020 |
| EP | 3114987 B1 | 8/2020 |
| EP | 3178516 B1 | 9/2020 |
| EP | 3738508 A1 | 11/2020 |
| EP | 3738509 A1 | 11/2020 |
| EP | 3340916 B1 | 12/2020 |
| EP | 3579908 B1 | 12/2020 |
| EP | 3749195 A1 | 12/2020 |
| EP | 3750475 A1 | 12/2020 |
| EP | 3768185 A1 | 1/2021 |
| EP | 2155301 B1 | 4/2021 |
| EP | 3432820 B1 | 4/2021 |
| EP | 3476331 B1 | 5/2021 |
| EP | 3579758 B1 | 5/2021 |
| EP | 2809254 B1 | 6/2021 |
| EP | 3508245 B1 | 7/2021 |
| EP | 3858277 A1 | 8/2021 |
| EP | 3892221 A1 | 10/2021 |
| EP | 3932343 A4 | 1/2022 |
| EP | 3791820 B9 | 4/2022 |
| JP | 4545384 B2 | 7/2010 |
| JP | 4887810 B2 | 2/2012 |
| JP | 4940332 B2 | 3/2012 |
| JP | 2012055602 A | 3/2012 |
| JP | 2012200509 A | 10/2012 |
| JP | 5154031 B2 | 2/2013 |
| JP | 5193190 B2 | 5/2013 |
| JP | 5372314 B2 | 12/2013 |
| JP | 2014014713 A | 1/2014 |
| JP | 5550150 B2 | 5/2014 |
| JP | 5762697 B2 | 6/2015 |
| JP | 5856712 B2 | 2/2016 |
| JP | 5908270 B2 | 4/2016 |
| JP | 5944331 B2 | 7/2016 |
| JP | 6050522 B2 | 12/2016 |
| JP | 2017051211 A | 3/2017 |
| JP | 2017104552 A | 6/2017 |
| JP | 6246742 B2 | 12/2017 |
| JP | 6342524 B2 | 6/2018 |
| JP | 6434495 B2 | 12/2018 |
| JP | 6445509 B2 | 12/2018 |
| JP | 6445742 B1 | 12/2018 |
| JP | 6466114 B2 | 2/2019 |
| JP | 6515084 B2 | 5/2019 |
| JP | 6528010 B1 | 6/2019 |
| JP | 6655655 B2 | 2/2020 |
| JP | 6776021 B2 | 10/2020 |
| JP | 6776025 B2 | 10/2020 |
| JP | 6786275 B2 | 11/2020 |
| JP | 6821812 B2 | 1/2021 |
| JP | 2021007772 A | 1/2021 |
| JP | 2021501011 A | 1/2021 |
| JP | 6843502 B2 | 3/2021 |
| JP | 6894004 B2 | 6/2021 |
| JP | 6920312 B2 | 8/2021 |
| JP | 6926306 B2 | 8/2021 |
| JP | 6932484 B2 | 8/2021 |
| JP | 6936872 B2 | 9/2021 |
| JP | 2021523755 A | 9/2021 |
| JP | 6980386 B2 | 11/2021 |
| JP | 2022020838 A | 2/2022 |
| WO | WO-9811933 A1 * | 3/1998 | ........ A61M 25/1002 |
| WO | 9843530 A1 | 10/1998 |
| WO | 0168178 A1 | 9/2001 |
| WO | 2008091197 A1 | 7/2008 |
| WO | 2015130829 A1 | 9/2015 |
| WO | 2017098198 A1 | 6/2017 |
| WO | 2018053148 A1 | 3/2018 |
| WO | 2018053164 A1 | 3/2018 |
| WO | 2018136741 A1 | 7/2018 |
| WO | 2019195439 A1 | 10/2019 |

\* cited by examiner

UNIFORM MAPPING BALLOON

CROSS-REFERENCE TO RELATED APPLICATIONS

This application claims the benefit of U.S. application No. 62/737,395, entitled "UNIFORM MAPPING BALLOON," filed 27 Sep. 2018, which is hereby incorporated by reference as though fully set forth herein.

BACKGROUND a. Field

The instant disclosure relates to devices and methods for a catheter, such as a mapping catheter.

b. Background Art

Catheters have been used for cardiac medical procedures for many years. Catheters can be used, for example, to diagnose and treat cardiac arrhythmias, while positioned at a specific location within a body that is otherwise inaccessible without a more invasive procedure. Mapping catheters can be used to measure the geometry of internal tissue within the body, and sometimes, to detect electrophysiological signals in the associated tissue. Navigating the mapping catheter to a desired location within the body for conducting such measurements can often be aided by use of a catheter having an adjustable size. The catheter can be adjusted to a small size for navigating to the measurement site and then be expanded for taking measurements within internal cavities of the tissue, such as atriums and ventricles of a heart. When at the measurement site, mapping catheters often include one or more sensors for detecting contact with the tissue or for detecting electrophysiological signals within the tissue. The respective location of the electrode in contact with the tissue or the signal detected using the electrode in contact with the tissue can be recorded and used for diagnostic purposes.

The foregoing discussion is intended only to illustrate the present field and should not be taken as a disavowal of claim scope.

BRIEF SUMMARY

The instant disclosure relates to a catheter device including a mapping balloon for diagnosing or treating cardiac arrhythmias, for example, mapping electrophysiological signals of tissue within the body. In particular, the mapping balloon can include a high density of electrodes uniformly dispersed thereon. As discussed herein, the mapping balloon can also be referred to as simply the balloon for short. In one embodiment, the catheter can include a catheter shaft and a mapping balloon configured for navigation within a body. The mapping balloon can be coupled to the catheter shaft, such as at a distal end of the catheter shaft. The mapping balloon can have an exterior surface including a plurality of predefined fold locations to arrange the mapping balloon between a collapsed configuration and an expanded configuration. In the collapsed configuration, the mapping balloon can include a first dimension, and in the expanded configuration the mapping balloon can have a second dimension. The second dimension can be greater than the first dimension. The first dimension and the second dimension can be measured transverse to a longitudinal axis of the catheter shaft. In an example, the predefined fold locations can be thermo-set fold locations in the exterior surface. In some examples, the predefined hinge locations can be living hinges within the exterior surface.

The mapping balloon can include an intermediate configuration between the collapsed configuration and the expanded configuration. In the collapsed configuration and the intermediate configuration, the exterior surface can include an outer facing portion and an inner fold portion. The outer facing portion and the inner fold portion can be defined by the predefined fold locations. In the intermediate configuration or the collapsed configuration, for example, at least a portion of the inner fold portion can be located closer to a longitudinal axis of the mapping balloon than the outer facing portion. The plurality of predefined fold locations can be configured for bending in a predictable manner between the collapsed configuration and the expanded configuration. In some examples, the mapping balloon can be inflatable and deflatable to adjust the mapping balloon between the collapsed configuration and the expanded configuration. A lumen can extend along the catheter shaft to transport a fluid to inflate or deflate the mapping balloon.

A plurality of electrodes can be located along the exterior surface of the mapping balloon to communicate electrical signals with an electronic control unit (ECU). In some examples, the plurality of electrodes can include primary electrodes and secondary electrodes. The primary electrodes can be located on the outer facing portion, and the secondary electrodes can be located on an inner fold portion. The primary electrodes can be configured to make first contact with tissue as the mapping balloon is adjusted from the collapsed configuration toward the expanded configuration. In an example, such as where the mapping balloon is in the intermediate configuration or the collapsed configuration, the primary electrodes can be configured to contact tissue, and the secondary electrodes can be configured to be positioned in a bloodflow. In an example, the mapping balloon can include an electrode at a distal end of the mapping balloon. The spacing between the electrodes, such as the primary electrodes, can be clinically uniform along the exterior surface, such as at least one outer facing portion. For instance, spacing between the primary electrodes along each respective outer facing portion can be clinically uniform as the one or more various outer facing portions move with respect to one another as the configuration of the mapping balloon changes. In various examples the spacing between the electrodes can be clinically uniform when the mapping balloon is in the collapsed configuration, in the expanded configuration, or in a configuration in between. In an example, the plurality of electrodes can be located at a distance from the predefined fold locations. The locations of the plurality of electrodes can follow a predictable path between the collapsed configuration and the expanded configuration. The catheter can include a plurality of traces. Each trace can be electrically coupled to at least one of the respective electrodes to communicate electrophysiological signals to the ECU.

In a further example, a system can operate the catheter including a mapping balloon. The system can include an input device, a memory, and a processor. The mapping balloon can include an exterior surface having a plurality of electrodes located thereon. The mapping balloon can include predictable shapes in various configurations. The various configurations can include a collapsed configuration, an expanded configuration, and any configuration therebetween. In some examples, the mapping balloon can include at least one predefined fold location along the exterior surface. In various examples, the mapping balloon includes a plurality of predefined fold locations. The predefined fold locations can be configured to bend to adjust the mapping balloon between the collapsed configuration and the expanded configuration. The mapping balloon can include an outer facing portion and an inner fold portion. In an example, the outer facing portion and the inner fold portion can be defined by the predefined fold locations and move in a predictable manner between the collapsed configuration and the expanded configuration.

The input device can be configured for communication with the mapping balloon. The input device can include any wired or wireless connection. The input device can be adapted to receive a position of a datum of the mapping balloon using a positioning system, such as an electronic or magnetic field-based positioning system. In an example, the input device can obtain a measured internal pressure of the mapping balloon. The memory can be configured to store internal pressure values. The internal pressure values can correspond to the predictable shapes of the mapping balloon at the various configurations.

The processor can be configured for communication with the memory and the input device. In an example, the processor can be adapted to identify the geometry of the balloon based on the measured internal pressure corresponding to one of the predictable shapes stored in the memory. Respective locations of the plurality of electrodes can be calculated by the processor based on the position of the datum and the identified geometry. In some examples, the electrodes that are in contact with the tissue can be identified. For instance, the electrodes that are in contact with the tissue (e.g., select electrodes of the plurality of electrodes) can be determined by the processor. In a further example, the processor can be configured to choose the select electrodes based on which respective electrodes are located along the outer facing portion. In an example, a geometric model of the tissue can be constructed based on the respective locations and the select electrodes.

In some examples, the input device can be further adapted to detect electrical characteristics at the respective electrodes. For instance, the electrical characteristics can include, but are not limited to, an electrical coupling index of the plurality of electrodes, an impedance value between two or more electrodes, a signal amplitude, or a voltage between two or more electrodes. Accordingly, the processor can be adapted to choose the select electrodes that are in contact with tissue based on the electrical characteristics. In an example, the processor can be configured to calculate respective locations of the plurality of electrodes based on detecting a location of one or more locational electrodes using the electric-field-based positioning system or the magnetic-field-based positioning system. In a further example, the input device can be adapted to detect respective electrophysiological signals at the respective electrodes. A geometric model of the tissue can be constructed based on the respective locations and electrical characteristics of the plurality of electrodes. In some examples, the processor can be further configured map the electrophysiological signals. For instance, the map of the electrophysiological signals can be shown on the geometric model of the tissue. In an example, the geometric model and the electrophysiological map can be presented on a display.

In another embodiment, a method for operating the catheter can include receiving, at an ECU, an electrical signal corresponding to a plurality of electrodes located along an exterior surface of a mapping balloon located at a distal end of the catheter. In an example, the mapping balloon can include at least one predefined fold location configured to bend for adjusting the mapping balloon between the collapsed configuration and the expanded configuration. An electrical characteristic at the plurality of electrodes can be detected, for instance, at the ECU. Using the ECU, the electrodes are in contact with tissue can be determined based on the respective electrical characteristics of the plurality of electrodes.

In various examples, determining which electrodes are in contact with the tissue can include comparing the relative impedance between two or more electrodes and measuring the electrical signal from selected electrodes that are associated with an impedance value that is below a threshold impedance value. Determining which electrodes are in contact with the tissue can include comparing an electrical coupling index of the plurality of electrodes and selecting to measure the electrical signal from selected electrodes that have an electrical coupling index that exceeds a threshold electrical coupling value. In an example, determining which electrodes are in contact with the tissue can include comparing a signal strength among the various electrodes and selecting to measure the electrical signal from selected electrodes that have a signal strength that exceeds a threshold strength value. Determining which electrodes are in contact with the tissue can include determining if two or more electrical contacts are electrically shorted to one another and excluding each electrode that is shorted from the electrodes calculated to be in contact with the tissue. In a further example, determining which electrodes are in contact with the tissue can include selecting electrodes locating on an outer facing portion of the exterior surface.

The location of the one or more electrodes in contact with the tissue can be calculated using the ECU. In an example, the electrophysiological signals can be measured using the electrodes that are determined to be in contact with the tissue. A map of the one or more electrodes in contact with the tissue can be generated using the ECU. The map can be configured for presentation on a display. In some examples, a graphical user interface of the display can be updated based on the one or more electrodes in contact with the tissue.

In yet another embodiment, a method for making a mapping balloon can include forming at least one predefined fold location along an exterior surface of a mapping balloon. The predefined fold location can be configured to bend the exterior surface of the mapping balloon between the collapsed configuration and the expanded configuration. The mapping balloon can include a first dimension in the collapsed configuration and a second dimension in the expanded configuration. In various examples, the second dimension greater than the first dimension. In an example, the predefined fold locations can be thermo-set into the exterior surface of the mapping balloon. In some examples, the predefined fold locations can be arranged to define an outer facing portion and an inner fold portion. At least a portion of the inner fold portion can be located closer to a longitudinal axis of the mapping balloon than the outer facing portion when the mapping balloon is in an intermediate or a collapsed configuration. In a further example, forming the at least one predefined fold location can include forming by a thinned cross section in exterior surface.

A plurality of electrodes can be disposed along the exterior surface of the mapping balloon. In an example, each of the plurality of electrodes can be configured to communicate an electrical signal with the ECU. Disposing the plurality of electrodes can include positioning the electrodes with a clinically uniform spacing along portions of the exterior surface. The spacing can be clinically uniform as measured along the exterior surface in the collapsed configuration or the expanded configuration. In an example, the electrodes can be disposed between the predefined fold locations along the exterior surface. The electrodes can be configured to follow a predictable path as the mapping balloon is adjusted between the collapsed configuration and the expanded configuration based on the position of the predefined fold locations and the location of the plurality of electrodes along the exterior surface. Configuring the electrodes to communicate an electrical signal to the electronic control unit can include electrically coupling a compliant circuit to one or more of the electrodes.

The foregoing and other aspects, features, details, utilities, and advantages of the present disclosure will be apparent from reading the following description and claims, and from reviewing the accompanying drawings.

DETAILED DESCRIPTION OF EMBODIMENTS

The instant disclosure relates to a catheter device including a mapping balloon for diagnosing or treating cardiac arrhythmias, for example, mapping electrophysiological signals of tissue within the body. In particular, the instant disclosure relates to a mapping balloon including an exterior surface with one or more predefined fold locations. A plurality of electrodes can be located along the exterior surface of the mapping balloon where locations of the plurality of electrodes can be calculable. For instance, the plurality of electrodes can follow a predictable path between a collapsed configuration and an expanded configuration of the mapping balloon. The present disclosure further describes a method of operating and a method of making the catheter with the mapping balloon. In particular the present disclosure includes a method for determining locations of one or more electrodes of the mapping balloon that are in contact with tissue. The method can further include, among other things, generating a geometry model or a map of electrophysiological signals of the tissue using the one or more electrodes, such as one or more electrodes that are determined to be in contact with the tissue. Details of the various examples of the present disclosure are described below with specific reference to the figures.

Figure 1:
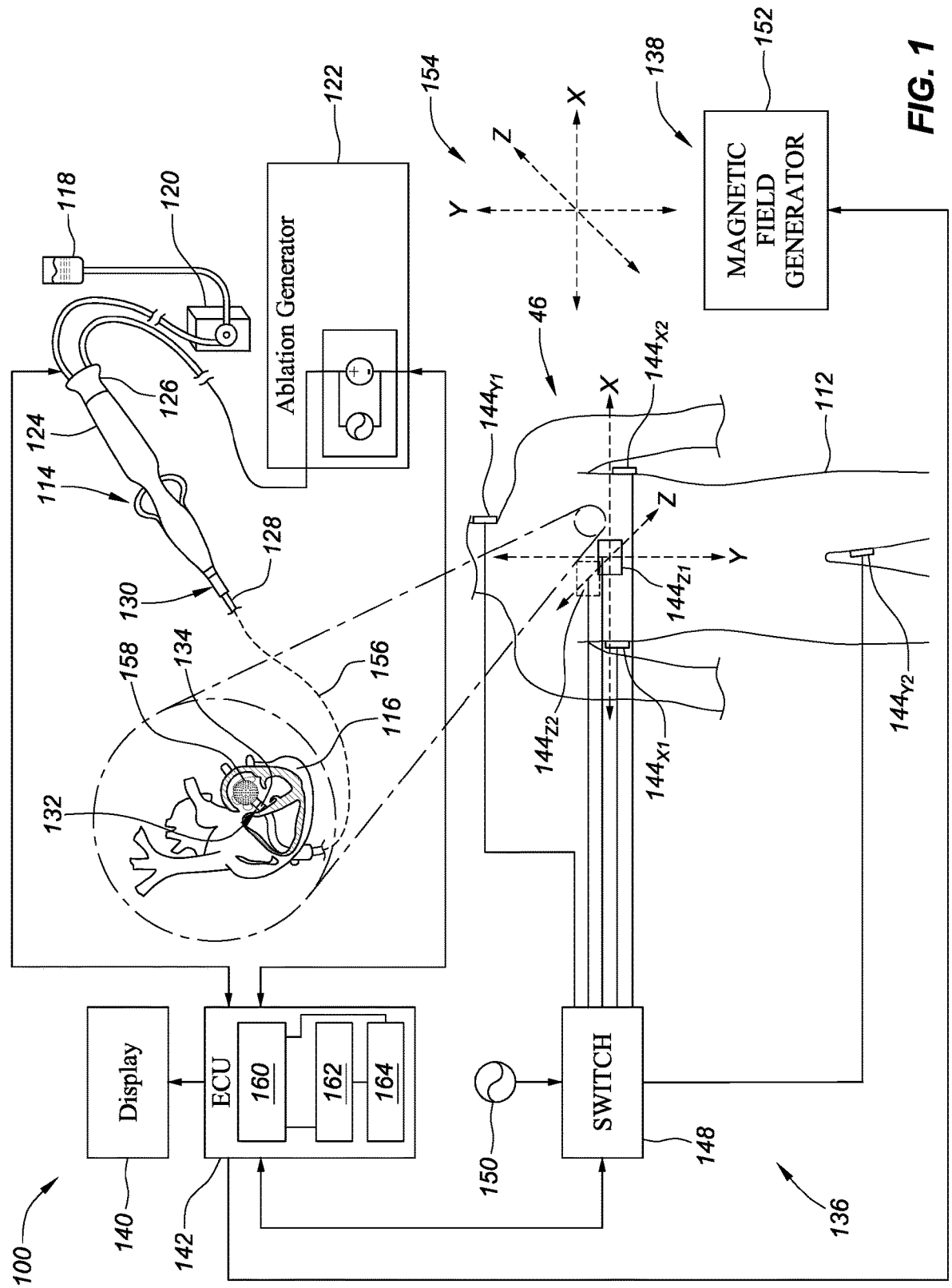
FIG. 1 is an example of a system for navigating a catheter within a body, according to an embodiment.

FIG. 1 illustrates one example of a system 100 for navigating and operating a medical device within a body 112. In the illustrated example, the medical device comprises a catheter 114 including a mapping balloon that is shown schematically entering a heart 158 that has been exploded away from the body 112. The catheter 114, in this example, is depicted as a catheter for modeling the geometry or mapping electrophysiological signals corresponding to cardiac tissue 116 in the body 112. It should be understood, however, that the system 100 can find application in connection with a wide variety of medical devices used within the body 112 for diagnosis or treatment. Further, it should be understood that the system 100 can be used to navigate medical devices used in the diagnosis or treatment of portions of the body 112 other than cardiac tissue 116. Further description of the systems and components are contained in U.S. patent application Ser. No. 13/839,963 filed on 15 Mar. 2013, which is hereby incorporated by reference in its entirety as though fully set forth herein.

The catheter 114 can include a handle 124, a cable connector or interface 126 at a proximal end of the handle 124, and a shaft 128 (also referred to herein as a catheter shaft). The shaft 128 can include a proximal end 130, a distal end 132. A balloon, such as a mapping balloon 158 can be coupled to the distal end 132. The handle 124 provides a location for the physician to hold the catheter 114 and can further provide means for steering or guiding the shaft 128 within the body 112. For example, the handle 124 can include means to change the length of one or more pull wires extending through the catheter 114 from the handle 124 to the distal end 132 of shaft 128. The construction of the handle 124 can vary.

The shaft 128 can be made from conventional materials such as polyurethane and can define one or more lumens configured to house and/or transport electrical conductors 156, fluids, or surgical tools. The shaft 128 can be introduced into a blood vessel or other structure within the body 112 through a conventional introducer. The shaft 128 can then be steered or guided through the body 112 to a desired location such as the tissue 116 using guide wires or pull wires or other means known in the art including remote control guidance systems. The shaft 128 can also permit transport, delivery, and/or removal of fluids (including irrigation fluids and bodily fluids), medicines, and/or surgical tools or instruments. It should be noted that any number of methods can be used to introduce the shaft 128 to areas within the body 112. This can include introducers, sheaths, guide sheaths, guide members, guide wires, or other similar devices. For ease of discussion, the term introducer will be used throughout.

In some examples, the system 100 can include a positioning system, a display 140, and an electronic control unit (ECU) 142. The ECU 142 can include, but is not limited to, a processor 164, a memory 162, and an input device 160. The processor 164 can include, but is not limited to, a central processing unit (CPU), graphics processing unit (GPU), microprocessor, application specific integrated circuit (ASIC), a field programmable gate array (FPGA), complementary metal-oxide-semiconductor (CMOS), or the like. In some examples, the memory 162 can include, but is not limited to, random-access memory (RAM), read-only memory (ROM), programmable read-only memory (PROM), erasable programmable read-only memory (EPROM), and electrically erasable programmable read-only memory (EEPROM), dynamic random-access memory (DRAM), static random-access memory (SRAM), Flash memory, or the like. The input device 160 can be wired or wireless interface for communicatively coupling the ECU 142 to the various components of the system 100, such as the catheter 114. For instance, the input device 160 can include a connector for coupling with one or more electrical wires or cables. In a further example, the input device 160 can include a wireless transceiver, such as an Ethernet, Bluetooth, Wi-Fi (e.g., 802.11), wireless local area network (WLAN), or other wireless communication interface.

Further examples of the system components are described below. The positioning system can include an electric-field-based positioning system 136, a magnetic-field-based positioning system 138, or the like. The positioning system, such as the electric-field-based positioning system, the magnetic-field-based positioning system, or a combination thereof, can be used to locate and detect the orientation of the mapping balloon 158 within the body 112. For instance, the location or orientation of the mapping balloon 158 can be based on a fiducial or location of one or more locational electrodes 134 (e.g. ring electrodes) of the mapping balloon 158. In an example, the fiducial or location of one or more locational electrodes of the mapping balloon can be used as a coordinate system or a datum of the mapping balloon 158. In a further example, the electric-field-based positioning system can be used to determine the location of one or more electrodes, for instance, one or more mapping electrodes (e.g., electrodes 304 as described further herein).

The positioning system, such as the electric-field-based positioning system 136 or the magnetic-field-based positioning system 138, is provided to determine the position and orientation of the catheter 114 and similar devices within the body 112. The position and orientation of the catheter 114 and similar devices within the body 112 can be determined by the system 136 and/or the system 138. The system 136 can comprise, for example, the EnSite™ NavX™ system sold by St. Jude Medical, Inc. of St. Paul, Minnesota, and described in, for example, U.S. Pat. No. 7,263,397 titled "Method and Apparatus for Catheter Navigation and Location Mapping in the Heart," the entire disclosure of which is hereby incorporated by reference as though fully set forth herein. The systems 136 and 138 can comprise, for example, the EnSite Precision™ system sold by St. Jude Medical, Inc., of St. Paul, Minnesota. The system 136 operates based upon the principle that when low amplitude electrical signals are passed through the thorax, the body 112 acts as a voltage divider (or potentiometer or rheostat) such that the electrical potential or field strength measured at one or more electrodes, such as locational electrodes 134, on the catheter 114 can be used to determine the position of the electrodes, and, therefore, of the catheter 114, relative to a pair of external patch electrodes using Ohm's law and the relative location of a reference electrode (e.g., in the coronary sinus).

In the configuration shown in FIG. 1, the electric-field-based positioning system 136 further includes three pairs of patch electrodes 144, which are provided to generate electrical signals used in determining the position of the catheter 114 within a three-dimensional coordinate system 146. The electrodes 144 can also be used to generate electrophysiology (EP) data (e.g., electrophysiological signals) regarding the tissue 116. To create axes-specific electric fields within body 112, the patch electrodes are placed on opposed surfaces of the body 112 (e.g., chest and back, left and right sides of the thorax, and neck and leg) and form generally orthogonal X, Y, and Z axes. A reference electrode/patch (not shown) is typically placed near the stomach and provides a reference value and acts as the origin of the coordinate system 146 for the navigation system.

In accordance with this exemplary system 136 as depicted in FIG. 1, the patch electrodes include right side patch $144_{X1}$, left side patch $144_{X2}$, neck patch $144_{Y1}$, leg patch $144_{Y2}$, chest patch $144_{Z1}$, and back patch $144_{Z2}$; and each patch electrode is connected to a switch 148 (e.g., a multi-plex switch) and a signal generator 150. The patch electrodes $144_{X1}$, $144_{X2}$ are placed along a first (X) axis; the patch electrodes $144_{Y1}$, $144_{Y2}$ are placed along a second (Y) axis, and the patch electrodes $144_{Z1}$, $144_{Z2}$ are placed along a third (Z) axis. Sinusoidal currents are driven through each pair of patch electrodes, and voltage measurements for one or more position sensors (e.g., locational electrodes 134) associated with the catheter 114 are obtained. The measured voltages are a function of the distance of the position sensors from the patch electrodes. The measured voltages are compared to the potential at the reference electrode and a position of the position sensors within the coordinate system 146 of the navigation system is determined.

The magnetic-field-based positioning system 138 in this example employs magnetic fields to detect the position and orientation of the catheter 114 within the body 112. The system 138 can include the GMPS system made available by MediGuide, Ltd. and generally shown and described in, for example, U.S. Pat. No. 7,386,339 titled "Medical Imaging and Navigation System," the entire disclosure of which is hereby incorporated by reference as though fully set forth herein. In such a system, a magnetic field generator 152 can be employed having three orthogonally arranged coils (not shown) to create a magnetic field within the body 112 and to control the strength, orientation, and frequency of the field. The magnetic field generator 152 can be located above or below the patient (e.g., under a patient table) or in another appropriate location. Magnetic fields are generated by the coils and current or voltage measurements for one or more position sensors associated with the catheter 114 are obtained. The measured currents or voltages are proportional to the distance of the sensors from the coils, thereby allowing determination of a position of the sensors within a coordinate system 154 of system 138.

The display 140 is provided to convey information to a physician to assist in diagnosis and treatment. The display 140 can comprise one or more conventional computer monitors or other display devices. The display 140 can present a graphical user interface (GUI) to the physician. The GUI can include a variety of information including, for example, an image of the geometry of the tissue 116, electrophysiology data (e.g., signals) associated with the tissue 116, graphs illustrating voltage levels over time for various locational electrodes 134, and images of the catheter 114 and other medical devices and related information indicative of the position of the catheter 114 and other devices relative to the tissue 116.

The ECU 142 provides a means for controlling the operation of various components of the system 100, including the catheter 114, the ablation generator 122, and magnetic generator 152 of the magnetic-field-based positioning system 138. The ECU 142 can also provide a means for determining the geometry of the tissue 116 (as discussed further herein), electrophysiology characteristics (e.g., signals) of the tissue 116, and the position and orientation of the catheter 114 relative to tissue 116 and the body 112. The ECU 142 also provides a means for generating display signals used to control the display 140.

As the catheter 114 moves within the body 112, and within the electric field generated by the electric-field-based positioning system 136, the voltage readings from the locational electrodes 134 change, thereby indicating the location of catheter 114 within the electric field and within the coordinate system 146 established by the system 136. The locational electrodes 134 can be adapted to communicate position signals to the ECU 142.

In some examples, the catheter 114 can be configured to deliver treatment as well as geometric modeling or electrophysiological mapping. For instance, the catheter 114 can include electrodes that are configured for ablation. In examples where the catheter 114 is configured for ablation, the catheter 114 can be optionally connected to a fluid source 118 for delivering a biocompatible irrigation fluid such as saline through a pump 120. The pump 120 can include a fixed rate roller pump or variable volume syringe pump with a gravity feed supply from fluid source 118 as shown. The catheter 114 can also be electrically connected to an ablation generator 122 for delivery of RF energy. The connector 126 provides mechanical, fluid, and electrical connections for conduits or cables extending from the pump 120 and the ablation generator 122. The catheter 114 can also include other conventional components not illustrated herein such as a temperature sensor, additional electrodes, and corresponding conductors or leads.

Figure 2:
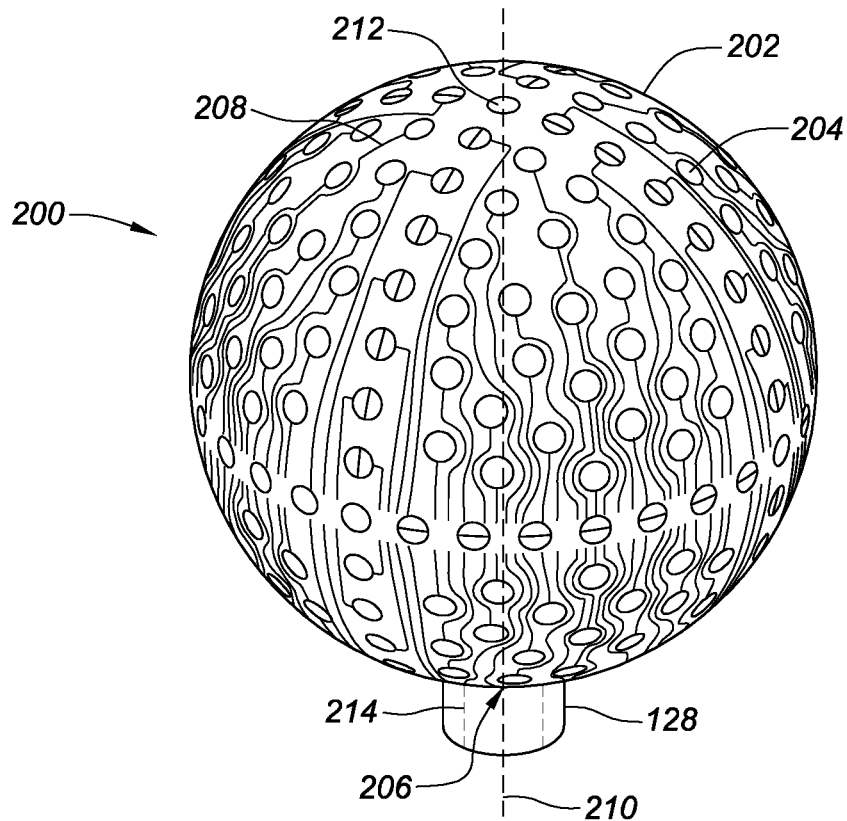
FIG. 2 is a perspective view of an example of a mapping balloon including a plurality of electrodes, according to an embodiment.

FIG. 2 is a perspective view of a mapping balloon 200 including a plurality of electrodes 204. The mapping balloon 200 can be located at a distal end 206 of the shaft 128. For instance, the mapping balloon 200 can be coupled to the distal end 206 of the shaft 128. A plurality of electrodes 204 can be located along an exterior surface 202 of the mapping balloon 200 as shown in the example of FIG. 2.

The electrodes 204 can include an electrically conductive material for receiving electrophysiological signals from tissue in contact of the electrodes 204. In some examples, the electrodes 204 can be electroplated, electrolessly plated, vapor deposited, chemically deposited, printed, or disposed on to the exterior surface 202 by other means. The electrodes can be densely distributed along the exterior surface. For instance, the electrodes can be distributed along the exterior surface with a center-to-center spacing or pitch of 1.0 mm. As shown in the example of FIG. 2, the electrodes 204 can be arranged on the exterior surface 202 with clinically uniform spacing. Clinically uniform spacing as described herein can refer to a spacing that is sufficiently uniform for geometric modeling or electrophysiological mapping or diagnosis for a clinical procedure. For instance, the center-to-center distance among the various electrodes 204 can preferably include a variation of less than twenty percent, preferably 0.2 mm or 0.1 mm or less. In an example, an electrode 212 can be located at the distal end of the mapping balloon 200. The clinically uniform spacing, in some examples, can facilitate electrophysiological mapping, such as omni-directional mapping of electrophysiological signals. Uniform spacing of electrodes (e.g., across and along the exterior surface of the mapping balloon) can increase the accuracy, precision, or a combination thereof of the electrophysiological mapping. For instance, the accuracy of an algorithm for direction mapping, such as omni-directional mapping, can be increased as a result of the uniform spacing of the electrodes.

The plurality of electrodes 204 can be electrically coupled to the ECU 142. In some examples, the electrodes 204 can be electrically coupled to the ECU 142 by one or more electrical conductors 208 (e.g., traces). For instance, the electrical conductors 208 can be coupled to respective electrodes 204 or each electrode 204 can be coupled to at least one respective electrical conductor 208. The electrical conductors 208 can be wires, conductive routing layers, electrical contacts (e.g., spring contacts or flat contacts), flexible circuit, or the like. In further examples, the electrodes 204 can be wirelessly coupled to the ECU 142. In some examples, the shaft 128 can include a lumen 214. In some examples, the lumen 214 can be aligned with the longitudinal axis 210 of the mapping balloon 200. One or more electrical conductors 208 can extend through the lumen 214 to electrically couple the electrodes 204 with the ECU 142. Accordingly the electrophysiological signals can be communicated to the ECU 142.

In a further example, the electrodes 204, the electrical conductors 208, or both can be disposed along a flexible or compliant substrate, and the substrate can be attached (e.g., bonded) to the exterior surface 202 of the mapping balloon 200. In some instances, the electrodes 204 or electrical conductors 208 can be constructed of a compliant conductive material. For example, the compliant conductive material can be a conductive ink, composite material having a flexible substrate with conductive particles embedded therein, or a conductive material having a strain relief feature configured to increase the extensibility of the conductive material.

At least some of the electrodes 204 of the mapping balloon 200 can be positioned to be in contact with tissue of the patient, such as tissue of the heart. Accordingly, the electrodes can be used to generate a geometric model of the tissue, an electrophysiological model (e.g., map) of the tissue, or a combination thereof. For example, the geometric model can include the physical shape and dimensions of the tissue, such as the tissue of the heart. In an example, contact with the tissue can be detected using the electrodes 204. The geometry of the tissue can be calculated based on a determined location of the electrodes 204 and the configuration of the mapping balloon 200. For instance, the ECU 142 can determine the geometry of the tissue based on the location and orientation of the mapping balloon 200 within the body, the determined geometry of the mapping balloon 200, and the location of at least some of the electrodes 204 on the exterior surface 202 of the mapping balloon 200.

In a further example, electrophysiological signals can be received at the electrodes 204 in contact with the tissue. The electrophysiological signals can be received at the ECU 142. Accordingly, the ECU 142 can be adapted to map the electrophysiological signals within the heart. In some examples, the electrophysiological signals can include, but is not limited to, electrical signals of the heart, muscle tissue, brain, stomach, arteries, nerves, lungs, or other electrophysiological signals. The electrophysiological signals can be mapped for presentation on a display. For instance, the electrophysiological signals can be presented in a graphical user interface. In some examples, the electrophysiological signals can be mapped and presented on the geometric model of the tissue. For instance, the electrophysiological signals can be assigned various indicia (e.g., icon, color, or the like) associated with a value of the electrophysiological signal. Accordingly, the electrophysiological signals can be used for electrocardiography, electroencephalography, electrocorticography, electromyography, or the like.

Figure 3:
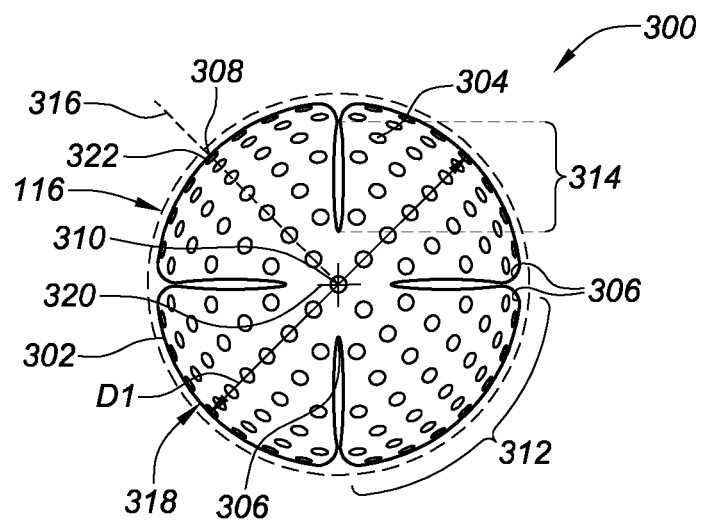
FIG. 3 depicts an example of a mapping balloon in the collapsed configuration, according to an embodiment.
Figure 4:
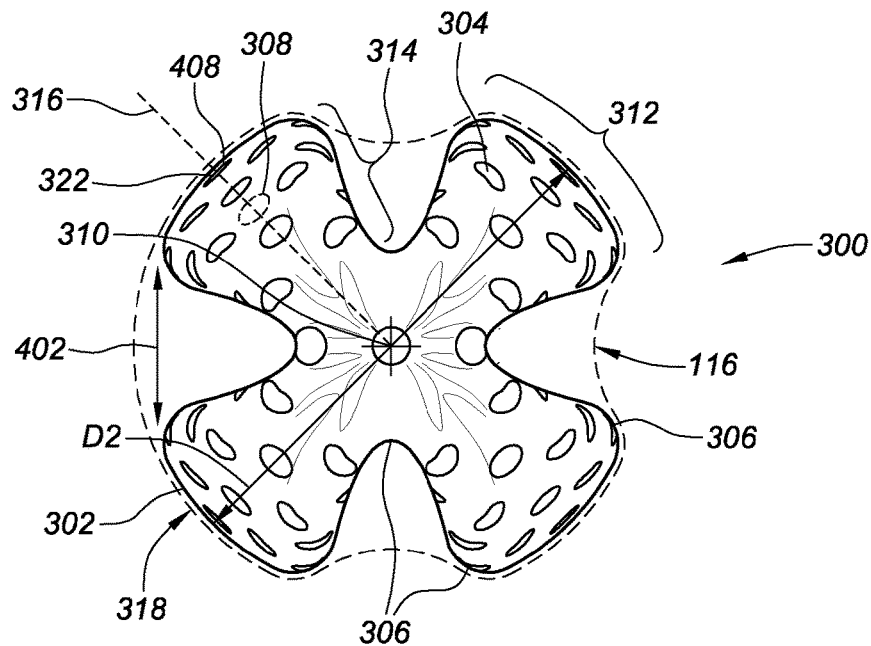
FIG. 4 illustrates an example of a mapping balloon in an intermediate configuration, according to an embodiment.
Figure 5:
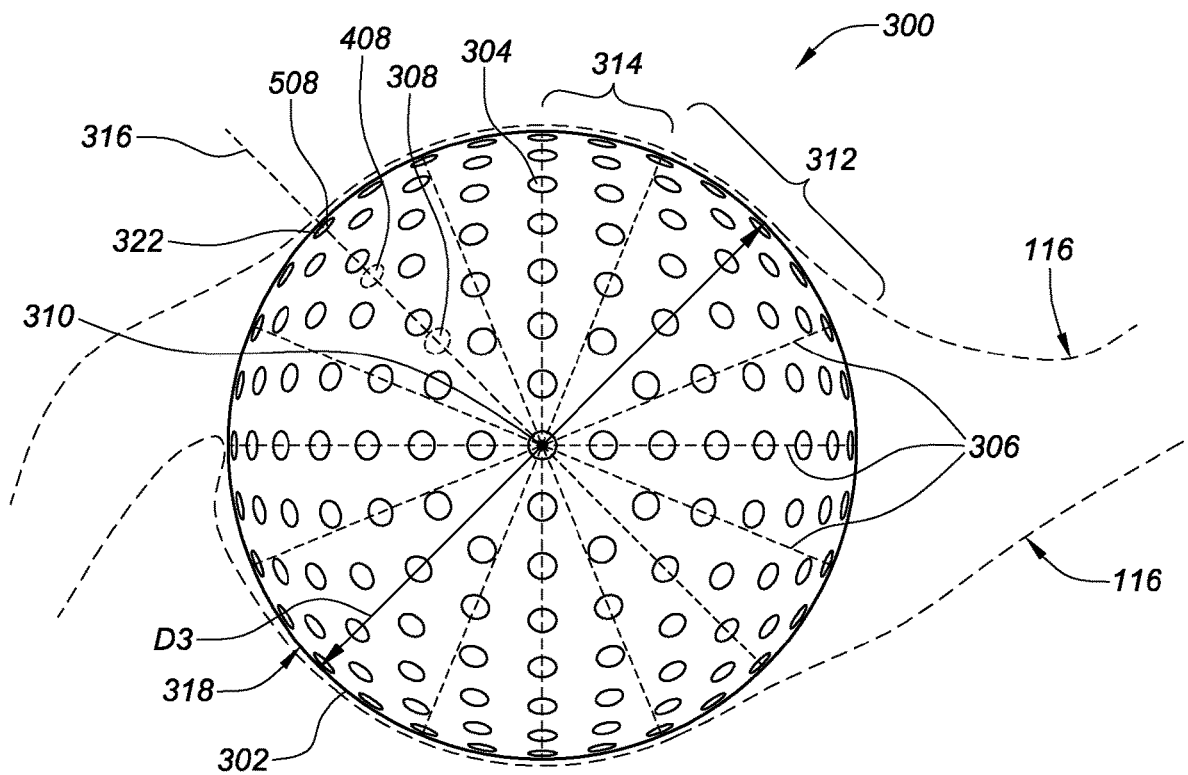
FIG. 5. depicts an example of a mapping balloon in an expanded configuration, according to an embodiment.

FIG. 3 depicts an example of the mapping balloon 300 in a collapsed configuration. The mapping balloon 300 can be adjusted between the collapsed configuration (as shown in the example of FIG. 3), an expanded configuration (as shown in the example of FIGS. 2 and 5), or any configuration therebetween, such as the intermediate configuration (as shown in the example of FIG. 4). A dimension of the mapping balloon 300, such as an overall dimension D1 can be smaller in the collapsed configuration as compared to the corresponding dimension of the mapping balloon in other configurations, such as the intermediate or expanded configurations. In an example, the dimension, such as the overall dimension D1, can be measured transverse to the longitudinal axis 310 (e.g., longitudinal axis 210 as shown in the example of FIG. 2). As used herein, the term overall dimension can describe the maximum dimension across the mapping balloon 300 as measured transverse to the longitudinal axis 310.

In an example, the mapping balloon 300 can be inflatable to adjust the configuration to the expanded configuration or the intermediate configuration. For instance, the mapping balloon 300 can be inflated with a gas or a liquid. Inflating the mapping balloon 300 with a liquid can mitigate the risk of causing bubbles within the circulatory system of a patient, in the event of a leak in the mapping balloon 300. When inflated or partially inflated, the mapping balloon 300 can be deflated to the collapsed configuration, or any configuration between the expanded configuration and the collapsed configuration. The gas or liquid used for inflation or deflation of the mapping balloon 300 can be transported through the lumen (e.g., the lumen 214 as shown in the example of FIG. 1). In other examples, the configuration of the mapping balloon 300 can be adjusted by mechanical, electro-mechanical, magnetic, or other means.

The mapping balloon 300 can include an exterior surface 302 having at least one predefined fold location. As shown in the example of FIG. 3, the mapping balloon 300 includes twelve predefined fold locations. The exterior surface can be configured to bend along the predefined fold location 306. In various examples, the predefined fold location 306 can include, but is not limited to, a thermo-set fold in the exterior surface 302, a living hinge, a thinned section of the exterior surface 302, a flexible material, an articulation, or other structure configured to bend at the predefined fold location 306. For instance, the predefined fold location 306 can be formed by heating and shaping predefined bends into the material of the exterior surface 302. In an example, the mapping balloon 300 can be blow molded. In a further example, the exterior surface 302 of the mapping balloon 300 can include a plurality of layers. The number, thickness, or bending modulus of the plurality of layers can be decreased along the predefined fold locations to facilitate bending of the exterior surface 302 at the predefined fold locations 306.

The exterior surface 302 can include at least one outer facing portion 312 and at least one inner fold portion 314. The outer facing portion 312 and the inner fold portion 314 can be defined by the predefined fold locations 306. For instance, the outer facing portion 312 can be located between two inner fold portions 306 (as shown in the example of FIG. 3) or the inner fold portion 314 can be located between two outer facing portions 312. In an example, the inner fold portions 314 can fold toward each other as the mapping balloon 300 is adjusted toward the collapsed configuration (e.g., like an accordion) to reduce the overall dimension D1 of the mapping balloon 300. Accordingly, the inner fold portion 314 can be located closer to the longitudinal axis 310 (extending out of the page in the example of FIG. 3) than the outer facing portion 312.

In some examples, the outer facing portions 312 and inner fold portions 314 can be structural. For instance, the mapping balloon 300 can be constructed of a material having sufficient strength to be self-supporting. Accordingly, the mapping balloon 300 can resist deformation (hold its shape) under its own weight. In the collapsed configuration, as shown example of FIG. 3, the inner fold portions 314 can be folded together and the outer facing portions 312 can define the external shape 318 of the mapping balloon 300. For instance, in the collapsed configuration, the predefined fold locations 306 along the edges of one outer facing portion 312 can be located adjacent to, or touching, the predefined fold locations 306 of an adjacently located outer facing portion 312. The external shape 318 can include, but is not limited to, a spherical (as shown in the example of FIG. 3), semi-spherical, ovoid shape, or other shape. Accordingly, the one or more outer facing portions 312 can have a contoured shape, such as a convex shape. In some examples, the mapping balloon 300 can include a single outer facing portion 312 that forms the external shape 318 of the mapping balloon 300.

The movement and relative positions of the various outer facing portions 312 and inner fold portions 314 can follow a repeatable pattern as the mapping balloon 300 is adjusted between the collapsed configuration and the expanded configuration. Accordingly, the position and shape of the outer facing portions 312 and inner fold portions 314 can be consistent in the collapsed configuration, expanded configuration, or at any configuration therebetween, such as the intermediate configuration. For example, the exterior surface 302 of the mapping balloon 300 can bend in a predictable manner based on the predefined fold locations 306. As used herein, predictable is defined as having a parameter that is calculably consistent within a useful tolerance for mapping applications. For instance, the useful tolerance can be a locational tolerance from an axis, coordinate system, datum, plane, other point, or other feature. In some examples, the location tolerance can be within 1.0 mm, or preferably 0.50 mm, 0.25 mm, or more preferably within 0.10 mm of the respective feature.

The electrodes 304 can be located along the outer facing portions 312, inner fold portions 314, or both. For instance, the electrodes 304 located on the outer facing portion 312 can be primary electrodes and the electrodes located on the inner fold portion 314 can be secondary electrodes. For example, the primary electrodes, being located along the outer facing portion 312, can be configured to make first contact with the tissue 116 as the mapping balloon 300 is adjusted from the collapsed configuration toward the expanded configuration. In some examples, the electrodes can be arranged in cliques. For instance, the primary electrodes 304, secondary electrodes, or both can include electrodes that are grouped together in a pattern. In some instances, the pattern can be repeating along the exterior surface of the mapping balloon. In other words, a clique can include a first, second, third, or further instance of the pattern. In the example of FIGS. 3-5, the tissue 116 is depicted for illustrative purposes only and does not represent any specific tissue in particular, but could be various arteries, veins, atriums and ventricles of the heart, or the like. In the example of FIGS. 3-5, one or more portions of the mapping balloon, such as the outer facing portions, the inner facing portions, or combinations thereof can be contact or separated from the tissue.

The location of the electrodes 304 along the exterior surface 302 can be calculated by the ECU 142. For instance, the location of the electrodes 304 can be calculated with respect to a datum 320 (e.g., coordinate system of the mapping balloon). In some examples the location of the electrodes 304 can be calculated based on various factors. The various factors can include, but are not limited to the size and shape of the various outer facing portions 312 and inner fold portions 314, the location of the electrode 304 along the respective outer facing portion 312 or inner fold portion 314, the configuration of the mapping balloon 300 (e.g., the collapsed, intermediate, or expanded configuration), or any combination thereof. For instance, the geometric shape of the balloon 300 can be known or calculable by the ECU 142 based on a known size and shape of the outer facing portions 312 and the inner fold portions 314, known locations of the predefined fold locations 306, and the structural material of the exterior surface 302. Accordingly, the location of the plurality of electrodes can be calculated based on the known geometry of the balloon 300. The known geometry of the balloon can be stored in the memory of the ECU 142 and can be calculated by the ECU for the various configurations of the balloon 300, such as the collapsed configuration, expanded configuration, or any configuration therebetween.

In the example of FIG. 3, where the mapping balloon 300 is the in the collapsed configuration, the electrodes 304 can include an electrode 322. The electrode 322 can be at a location 308. In some examples, the electrodes 304 can be located along the outer facing portion 312 or the inner fold portion 314 at a distance from the predefined fold locations 306. Locating the electrodes 304 at a distance from the predefined fold locations 306 can reduce variability of the location of the respective electrodes 304 along the predefined fold locations 306. For instance, variability related to the geometry of the predefined fold locations 306 and the respective locations of the electrodes 304 thereon can be reduced. In further examples, the electrodes 304 can be located along the predefined fold locations 306 for the collection of electrophysiological signal measurement or geometry modeling along the predefined fold locations 306.

The electrodes 304 can be configured to receive and facilitate communication of electrical or electrophysiological signals to the ECU 142. As previously described, the spacing between the electrodes 304, such as the primary electrodes, can be clinically uniform along at least one outer facing portion, such as the outer facing portion 312 (e.g., as measured along the outer facing portion 312). For example, the center-to-center distance among the various electrodes 304 as measured along the outer facing portion can preferably include a variation of less than 0.2 mm or less. In an example, the spacing among the secondary electrodes along the inner fold portions 314 can also be clinically uniform. In other words, the spacing between electrodes located on different outer facing portions can change as the configuration of the mapping balloon is adjusted, and the spacing among electrodes along the respective outer facing portions or inner facing portions can be clinically uniform. Accordingly, the mapping balloon 300 can measure the electrophysiological signals or geometric locations along the tissue at a spatial resolution corresponding to the spacing of the electrodes 304 along the outer facing portion 312 or the inner fold portion 314. In the example of FIG. 3, the electrophysiological signals or geometric locations can be measured by the primary electrodes along the outer facing portion 312. Having calculable locations of the electrodes 312 (e.g., with respect to the datum 320) can improve the accuracy or precision of measuring the location or the electrodes 304 or electrophysiological signals with the ECU 142 and generating an accurate and precise electrophysiological map or geometric model based on the measurements. The clinically uniform spacing among the electrodes 304 can facilitate the ECU 142 in calculating the respective locations of the various electrodes 304. Accordingly, measuring the electrophysiological signals or the geometric location of the electrodes 304 using the mapping balloon 300 can increase the accuracy and precision of the electrophysiological signal or geometry map.

FIG. 4 illustrates an example of the mapping balloon 300 in a partially collapsed configuration (also referred to herein as the intermediate configuration). As previously stated, the mapping balloon 300 in the intermediate configuration can include a dimension, such as an overall dimension D2, that is between the overall dimension D1 of the mapping balloon in the collapsed configuration and the overall dimension (e.g., D3 as shown in FIG. 5) of the expanded configuration. As shown in the example of FIG. 4, the inner fold portions 314 and outer facing portions 312 can be moved outward from the datum 320 as compared to the collapsed configuration shown in the example of FIG. 3. In an example, the predefined fold locations 306 can be partially unbent as compared to the collapsed configuration. As shown in the example of FIG. 4, the outer facing portions 312 (e.g., the predefined fold locations 306 adjacent to the respective outer facing portions 312) can be separated by a gap 402.

Generally, a typical balloon, such as an elastic balloon, can inflate or deflate in an unpredictable manner. For instance, the surface of the typical balloon can crease unpredictably when the typical balloon is not inflated at a pressure to provide tension on the surface. Where the typical balloon includes a plurality of electrode contacts disposed along the surface of the balloon, the spacing between the electrode contacts as well as the relative position of the electrode contacts, or the position of the electrode contacts with respect to a common datum, can be inconsistent or not predictably calculable. For example, the spacing among the electrode contacts can vary as the typical balloon is inflated the spacing between electrode contacts can increase or decrease as a result of the elastic properties of the typical balloon material or as a result of the folding geometry of the typical balloon. In a further example, the relative position of the electrode contacts can change in an unpredictable or incalculable manner as the typical balloon folds or unfolds somewhat randomly during inflation or deflation. For instance, the typical balloon may not fold or unfold consistently for determining the relative position of the electrode contacts in a repeatable manner. Accordingly, the relative position of electrode contacts along the typical balloon can have random variability that inhibits the calculation of the position of each electrode contact, especially when the typical balloon is in a deflated or partially deflated configuration. This random variability can, in some instances, reduce the accuracy or precision of the mapping of the electrophysiological signals, or a combination thereof.

The mapping balloon of the present disclosure, such as the mapping balloon 300, can have geometry that adjusts between the collapsed configuration and the expanded configuration predictably to facilitate calculation of the mapping balloon geometry. For instance, as previously discussed, the outer facing portions 312 and inner fold portions 314 can move in a consistent, repeatable, and calculable pattern between the collapsed configuration and the intermediate configuration. Accordingly, the size, shape, and position of the outer facing portions 312 and the inner fold portions 314 can be calculated by the ECU 142.

In an example, the outer facing portions 312 can have a contoured shape based on the external shape 318 of the mapping balloon 300 (e.g., spherical, ovoid, prolate, or the like). In some instances, the outer facing portions 312 or inner fold portions 314 can change shape between the various configurations. For example, a curvature of the contour shape can change as the mapping balloon 300 is adjusted among the various configurations. In an example, the curvature (e.g., radius) of the outer facing portion 312 can increase as the mapping balloon 300 is adjusted from the collapsed configuration to the intermediate configuration and then the expanded configuration. As the position of the respective outer facing portions 312 and inner fold portions 314 can be predictably calculated by the ECU 142 at the various configurations, the curvature (and thus external shape 318) can also be predictably calculated. Accordingly, the overall dimension (e.g., D2) and the external shape 318 of the mapping balloon 300 can be calculable by the ECU 142.

The locations of the plurality of electrodes 304 can follow a predictable path 316 between the collapsed configuration and the expanded configuration. For instance, the electrodes at the respective configurations can be consistently calculable by the ECU 142. In various examples, the predictable path 316 can be calculated by the ECU 142 based on the location of the electrode 322 along the exterior surface 302 at the collapsed configuration, the expanded configuration, and any location therebetween (e.g., the intermediate configuration). In some examples, the predictable path 316 and the location of the various electrodes 304 can be calculable based on the size, shape, position, or curvature of the respective outer facing portion 312 or inner fold position 314. In an example, the location of the electrode, such as the electrode 322, along the predictable path 316 can be calculated using interpolation or other estimation means. As previously described, the location of the various electrodes 304 can be measured with respect to a datum, such as the datum 320.

In an example, each of the electrodes 304 along the outer facing portion 312 (the primary electrodes) can be located progressively further away from the longitudinal axis 310 of the mapping balloon 300 as the mapping balloon 300 is adjusted from the collapsed configuration to the expanded configuration. For example, the electrodes 304, such as the electrode 322, can move along the predictable path 316. The location 308 of the electrode 322, as located in the collapsed configuration, is shown in phantom line for reference. In the intermediate configuration, the electrode can have a location 408 along the predictable path 316.

In an example, the electrodes 204 in the intermediate configuration can be arranged in a clinically uniform spacing as measured along the exterior surface 302, similar to in the collapsed configuration. In some examples, where the exterior surface 302 includes a contoured shape, the clinically uniform spacing can take into account the curvature of the outer facing portion 312.

As shown in the example of FIG. 4, the at least some of the primary electrodes (e.g., electrodes 304 located along the outer facing portion 312) can be configured to make contact with the tissue 116. For instance, the primary electrodes can make first contact with the tissue 116 as the overall dimension D2 of the mapping balloon 300 increases according to the adjustment of the mapping balloon 300 from the collapsed configuration toward the expanded configuration. In the intermediate configuration, the secondary electrodes (e.g., electrodes 304 located along the one or more inner fold portions 314) can be separated from the tissue 116. For instance, where the mapping balloon 300 is within the circulatory system of the patient, the secondary electrodes can be located in the bloodflow.

The ECU 142 can determine which of the primary electrodes are in contact with the tissue 116 based on the electrical characteristics measured at the respective primary electrodes or the location of the respective primary electrodes. In an example, the primary electrodes can be estimated to be in contact with the tissue 116 whereas the secondary electrodes are estimated to be separated from the tissue 116. In some examples, the electrical characteristic can include, but is not limited to, an electrical coupling index, impedance value (e.g., a comparative impedance value), signal strength (e.g., signal voltage, amperage, or power), an electrophysiological signal, another electrical characteristic, or any combination thereof. For instance, the ECU 142 can measure the electrical coupling index or impedance among various electrodes 304 and determine which of the respective electrodes 304 are in contact with the tissue 116 based on a threshold electrical coupling index or impedance value. In a further example, the ECU 142 can determine which of the respective electrodes 304 are in contact with the tissue 116 based on the measured strength of the electrophysiological signal measured at the respective electrodes. For instance, electrodes 304 having greater signal strength can be determined to be in contact with the tissue 116. In some examples, contact force with the tissue 116 can be measured using the electrical characteristic of the respective electrodes 304.

In some examples, the ECU 142 can map the geometry of the tissue 116 based on the respective locations of the plurality of electrodes 304 determined to be in contact with the tissue 116. For instance, the location of one or more electrodes 304 (e.g., with respect to the datum 320) in contact with the tissue 116 can be recorded. Accordingly, a geometric model of the tissue 116 can be generated based on the plurality of electrode locations (e.g., location 308, 408). In a further example, the electrophysiological signals can be measured at the electrodes 304 in contact with the tissue 116. Accordingly, the electrogram map can be generated along the portion of the tissue in contact with one or more of the primary electrodes. In a further example, the ECU can analyze the electrical characteristics of the electrodes based on the arrangement of the electrodes in cliques. For instance, the ECU can perform calculations for modeling the geometry or mapping electrophysiological signals, such as those disclosed in the international application PCT/US2015/017582, filed on Feb. 25, 2015, which is incorporated herein by reference in its entirety.

FIG. 5 depicts an example of the mapping balloon 300 in the expanded configuration. In the expanded configuration, the predefined fold locations 306 can be unbent to align the outer facing portions 312 and inner fold portions 314. For instance, the outer facing portions 312 and inner fold portions 314 can be aligned (e.g., tangent or near tangent) in a spherical, ovoid, prolate, or other arrangement to define the exterior shape 318 of the mapping balloon 300. In an example, an angle A between the outer facing portion 312 and one or more inner fold portions 314 can be preferably between 120 to 150 degrees, or more preferably between 100 to 170 degrees, or more preferably yet near 180 degrees. For instance, the angle A in the expanded configuration can be increased as compared to the angle in the collapsed (e.g., near 90 degrees) or inter mediate configurations (between 90 and 180 degrees, such as 135 degrees). A dimension of the mapping balloon 300, such as an overall dimension D3, transverse to the longitudinal axis 310 of the mapping balloon 300, can be larger than the corresponding dimension (e.g., D1 and D2) of the mapping balloon 300 in other configurations, such as the collapsed configuration or the partially collapsed (intermediate) configuration. In an example, the dimension D3 can be configured to fit within various locations of a human heart. In one example, the balloon can include a dimension D3 of 10.0 mm or less.

In the example of FIG. 5, the electrodes, such as the electrode 322 can be at location 508 along the predictable path 316. The location 408 (of the electrode 322 in the intermediate configuration) and the location 308 (of the electrode 322 in the collapsed configuration) are shown in phantom line for reference. In the example of FIG. 5, the secondary electrodes (e.g., electrodes 304 located along the inner fold portions 314) can be positioned for contact with the tissue 116. The expanded configuration can present more electrodes 304 for contact with the tissue 116, thus providing for measurement of a larger mapping area in comparison to the intermediate and collapsed configurations. Accordingly, a greater number of simultaneous electrophysiological signal measurements or a greater number of geometry mapping measurements can be collected by the ECU 142. In another example, the mapping balloon 300 can map larger anatomical features due to the greater overall dimension D3.

Figure 6:
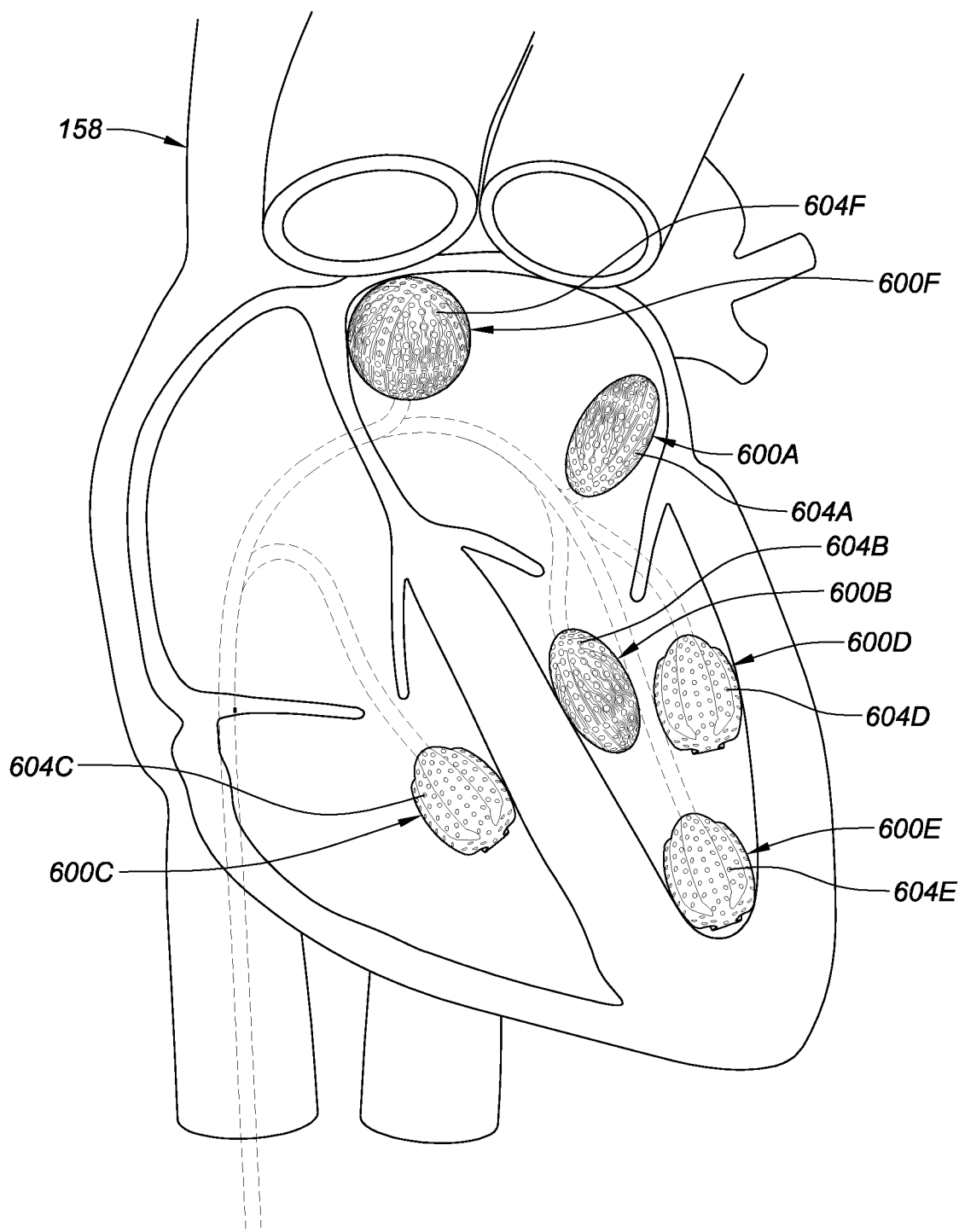
FIG. 6 is a cross section of an example of a heart with a plurality of mapping balloons located at various locations therein, according to an embodiment.

FIG. 6 is a cross section view of a heart, such as the heart 158, and a plurality of mapping balloons 600A-F located at various positions within the heart 158. While depicted without an introducer in the example of FIG. 6, the mapping balloons 600A-F can be used with a catheter (e.g., catheter 114) and an introducer, such as the Agilis™ steerable introducer by Abbott Laboratories, Inc. of Lake Bluff Ill. The mapping balloons 600A-F can be adjusted at various configurations, such as the collapsed configuration, intermediate configuration, or expanded configuration at different locations within the heart 158 (e.g., left or right ventricals or atriums) or within the vascular structure (e.g., inferior vena cava, aorta, or the like) connected to the heart 158. In some instances, the exterior surface (e.g., the exterior surface 302 as shown and described herein) of the mapping balloons 600A-F, and at least some of the respective electrodes 604A-F thereon (e.g., electrodes 304 as shown and described herein), can be in contact with tissue, such as the tissue of the heart 158. For instance, the mapping balloon 600A can be located at first position within a vascular structure connected to the heart, such as the left pulmonary vein, as shown in the example of FIG. 6. At the first position, the mapping balloon 600A can be in the collapsed configuration to reduce the overall dimension of the mapping balloon 600A. Accordingly, the collapsed configuration can facilitate transport of the mapping balloon 600A through the vascular structure. For instance, in the collapsed configuration, the mapping balloon 600A can include a size that can fit within the introducer. In a further example, the collapsed configuration can facilitate geometric modeling electrophysiological mapping within geometry of the tissue (e.g., heart 158) that is smaller than the overall dimension (e.g., overall dimensions D2 and D3 as shown and described herein) of the expanded configuration or some of the intermediate configurations. A further example of a balloon 600B in the collapsed configuration is shown along the wall of the left ventricle. The balloon 600B can be inserted into the left ventricle through the interventricular septum as shown.

The intermediate configuration is shown in the example of the mapping balloons 600C-E. In the intermediate configuration, the mapping balloons 600C-E can include an overall dimension, such as dimension D2, that is greater than the overall dimension D1 of the collapsed configuration (e.g., mapping balloon 600A or 600B) and smaller than the overall dimension D3 of the mapping balloon 600F in the expanded configuration. The overall dimension D2 of the intermediate configuration can provide contact between one or more of the respective electrodes 604C-E along the outer facing portions (e.g., outer facing portions 312) of the mapping balloons 600C-E and the tissue. Accordingly, the mapping balloons 600C-E can fit into regions of the heart 158 that are narrow or restricted, such as regions that are too small for the overall dimension D3 of the mapping balloon 600F in the expanded configuration. For instance, in the example of FIG. 6, the mapping balloon 600C is shown in the right ventricle, the mapping balloons 600D and 600E are shown in the left ventricle of the heart 158. For instance, the balloon 600D can be positioned at the left atrioventricular valve. The balloon 600E is shown at the trabeculae or the wall junction under the left atrioventricular valve. The predefined fold locations (e.g., predefined fold locations 306) can provide for consistent folding of the exterior surface between the collapsed configuration and the expanded configuration and can provide for predictable and calculable locations of the respective electrodes 604C-E with respect to the datum of the mapping balloon. Accordingly, the quality (e.g., accuracy and precision) of the geometry or electrophysiological signal mapping conducted using the mapping balloon can be increased.

In the expanded configuration, the mapping balloon 600F can have an overall dimension D3 that is larger than the overall dimensions D1, D2, of the intermediate or collapsed configurations. Accordingly, the mapping balloon 600F can span a wider distance within the geometry of the tissue. For instance, the mapping balloon 600F can be located in one of the atriums of the heart 158 or near one of the heart valves, as shown in the example of FIG. 6. As shown in the example of the mapping balloon 600F, at least some of the electrodes 604F, such as the secondary electrodes (e.g., electrodes 304 located along the one or more inner fold portions 314) can be in contact with the tissue as well as the primary electrodes (e.g., electrodes 304 located along the one or more outer facing portions 312). In some examples the mapping balloon 600F can be sized and shaped to fill an atrium or ventricle of the heart 158. The electrodes in contact with the tissue can have clinically uniform spacing as measured along the portions of the exterior surface in contact with the tissue (e.g., outer facing portions or inner fold portions). Thus, the mapping balloon 600F can be used to map a larger surface area of the tissue as compared to the collapsed or intermediate configurations.

In some examples, increasing the overall dimension can also increase the contact force between the electrodes and the tissue. For instance, increasing the contact force can decrease the contact resistance between the tissue and the electrical contact. Accordingly, increasing the contact force can provide for increased electrophysiological signal detection at the electrode. In a further example, a target contact force value can be achieved by adjusting the configuration of the mapping balloon. For instance, the target contact force can be less than the maximum contact force.

In various examples, a system (e.g., the ECU 142 shown in FIG. 1 and described herein) can operate a catheter, such as the catheter 114. The catheter can include a mapping balloon, such as the mapping balloon 158, 300, or 600A-F previously described in the examples herein and shown in FIGS. 1-6. The system can include an input device (e.g., input device 160), a memory (e.g., memory 162), and a processor (e.g., processor 164), as described herein.

As previously described, the mapping balloon can include an exterior surface having a plurality of electrodes located thereon. The mapping balloon can include predictable shapes in various configurations. In some examples, the various configurations can include a collapsed configuration, an expanded configuration, a configuration therebetween, or a combination thereof. In some examples, the mapping balloon can include at least one predefined fold location along the exterior surface. In various examples, the mapping balloon includes a plurality of predefined fold locations. The predefined fold locations can be configured to bend to adjust the mapping balloon between at least the collapsed configuration and the expanded configuration. The mapping balloon can include an outer facing portion and an inner fold portion. In an example, the outer facing portion and the inner fold portion can be defined by the predefined fold locations and move in a predictable manner between the collapsed configuration and the expanded configuration.

The input device can be configured for communication with the mapping balloon. For instance, the input device can include a connector for electrically coupling the electrodes of the mapping balloon to the system with one or more wires. In a further example, the input device can include any wired or wireless connection, as described herein. The input device can be adapted to receive a position of a datum of the mapping balloon using an electronic or magnetic field-based positioning system, such as the electric-field-based positioning system 136 or the magnetic-field-based positioning system 138 as described further herein. The input device can detect a configuration of the mapping balloon. For instance, in various examples the configuration of the mapping balloon can be detected by various inputs including, but not limited to, measuring the internal pressure of the mapping balloon, detecting the location of one or more locational electrodes (e.g., using electric-field-based positioning system or the magnetic-field-based positioning system), receiving an input from another type of position sensor (e.g., mechanical position sensor), measuring electrical parameters among the electrodes (e.g., electrical coupling index), or the like. In an example, the input device can obtain a measured internal pressure of the mapping balloon. For instance, the system can be communicatively coupled to a pressure sensor for measuring the internal pressure of the mapping balloon and transceiving a pressure signal to the system through the input device. The memory can be configured to store internal pressure values. The internal pressure values can correspond to the predictable shapes of the mapping balloon at the various configurations. For instance, the geometry (e.g., shape) of the balloon of the collapsed configuration, expanded configuration, or various configurations therebetween, can be stored in the memory. The various geometries can be associated with respective input corresponding to a detected configuration of the mapping balloon, such as the internal pressure values or other inputs described herein.

The processor can be configured for communication with the memory and the input device. In an example, the processor can be adapted to identify the geometry of the balloon based on the input corresponding to a detected configuration of the mapping balloon, such as the measured internal pressure, corresponding to one of the predictable shapes stored in the memory. Respective locations of the plurality of electrodes can be calculated by the processor based on the position of the datum and the identified geometry. For instance, with the internal pressure value, the processor can calculate the location of the plurality of electrodes along the exterior surface of the balloon based on the identified geometry. Using the position of the datum received at the input device, the processor can then determine the location of the plurality of electrodes, such as the location of the plurality of electrodes in three-dimensional space (e.g., with respect to the datum). In some examples, the electrodes that are in contact with the tissue can be identified. For instance, the electrodes that are in contact with the tissue (e.g., select electrodes of the plurality of electrodes) can be determined by the processor. For instance, the electrical characteristics of one or more electrodes, the location of the one or more electrodes (e.g., position along the exterior surface), or other means can be used to identify which electrodes are in contact with the tissue. In a further example, the processor can be configured to determine the select electrodes based on which respective electrodes are located along the outer facing portion. For instance, the electrodes on the outer facing portion can be determined to be the select electrodes. In an example, the electrodes along the outer facing portion can have a higher likelihood of being in contact with the tissue, as compared to the electrodes located along the inner fold portions. Accordingly, a geometric model of the tissue can be constructed based on the respective locations and the select electrodes.

In some examples, the input device can be further adapted to detect electrical characteristics at the respective electrodes. For instance, the electrical characteristics can include, but are not limited to, an electrical coupling index of the plurality of electrodes, an impedance value between two or more electrodes, a signal amplitude, a voltage between two or more electrodes (e.g., including one or more of the patch electrodes 144), or the like. Accordingly, the processor can be adapted to determine the select electrodes that are in contact with tissue based on the electrical characteristics. In an example, the processor can be configured to calculate respective locations of the plurality of electrodes based on detecting a location of one or more locational electrodes using the electric-field-based positioning system (e.g., electric-field-based positioning system 136) or the magnetic-field-based positioning system (e.g., or the magnetic-field-based positioning system 138). In a further example, the input device can be adapted to detect respective electrophysiological signals at the respective electrodes. A geometric model of the tissue can be constructed based on the respective locations and electrical characteristics of the plurality of electrodes. In some examples, the processor can be further configured map the electrophysiological signals. For instance, the map of the electrophysiological signals can be shown on the geometric model of the tissue. The geometric model and the electrophysiological map can be presented on a display. For instance, the display can include, but is not limited to, a light emitting diode (LED) display, liquid crystal display (LCD), or other type of electronic display.

In describing the following methods 700 and 800, reference is made to one or more components, features, functions, and processes previously described herein. Where convenient, reference is made to the components, features, processes and the like with reference numerals. Reference numerals provided are exemplary and are nonexclusive. For instance, features, components, functions, processes, and the like described in the methods 700 or 800 include, but are not limited to, the corresponding numbered elements provided herein. Other corresponding features described herein (both numbered and unnumbered) as well as their equivalents are also considered.

Figure 7:
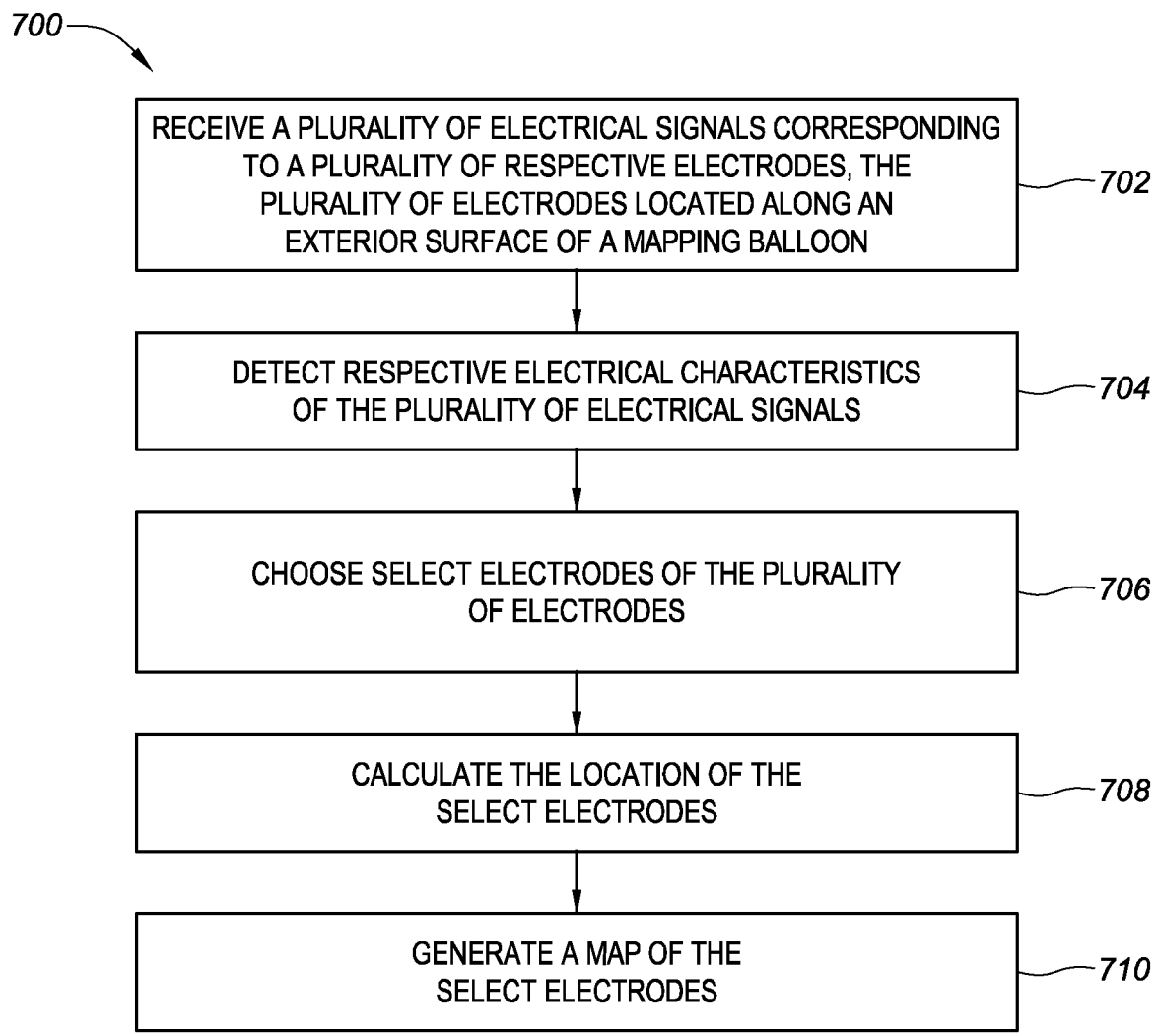
FIG. 7 is an example of a method for operating a catheter including a mapping balloon, according to an embodiment.

FIG. 7 is an example of a method 700 for operating a catheter including a mapping balloon, such as the mapping balloon 158, 300, or 600A-F previously described in the examples herein and shown for instance in FIGS. 1-6. In an example, the catheter can be operated by a system, such as the system 100 shown in the example of FIG. 1. At 702, a plurality of electrical signals can be received at an electronic control unit (ECU), such as the ECU 142. The electronic signals can correspond to a plurality of respective electrodes (e.g., electrodes 304) located along an exterior surface (e.g., exterior surface 318) of the mapping balloon. In an example, the mapping balloon can be located at a distal end of a catheter, such as catheter 114 as previously described herein. The exterior surface of the mapping balloon can include one or more predefined fold locations, such as predefined fold locations 306 as described herein. The predefined fold locations can bend for adjusting the mapping balloon between a collapsed configuration (e.g., the collapsed configuration shown in the example of FIG. 3) and an expanded configuration (e.g., the expanded configuration shown in the example of FIG. 5). In an example, the plurality of electrodes can be electrically coupled to the ECU through respective electrical conductors.

At 704, respective electrical characteristics of the plurality of electrical signals can be detected. For instance, the respective electrical characteristics can include, but are not limited to, an electrical coupling index, impedance value (e.g., a comparative impedance value), signal strength (e.g., signal voltage, amperage, or power), frequency, an electrophysiological signal, another electrical characteristic, or any combination thereof. For instance, the ECU can measure the electrical coupling index or impedance among various electrodes. In an example, an internal pressure of the mapping balloon can be adjusted to increase the contact force between one or more of the electrodes and the tissue. For instance, the pressure can be increased to decrease the electrical resistance between the electrodes and the tissue. In some examples, plaque can increase the electrical resistance and increasing the contact force can facilitate detection of the electrical characteristic measured from the tissue having plaque.

At 706, select electrodes can be chosen for measurement of geometry or electrophysiological signals corresponding to tissue using the electronic control unit. For instance, the select electrodes for mapping geometry or mapping electrophysiological signals can be chosen based upon the location of the electrodes on the mapping balloon. For example, the primary electrodes located on the outer facing portions or the secondary electrodes located on the inner fold portions can be chosen independently for measurement of the geometry or electrophysiological signals. In some examples, all of the electrodes can be chosen for measurement. Where the electrodes are not in contact with tissue, electrophysiological signals can be measured within the heart from the blood pool. In other examples, select electrodes that are in contact with tissue can be chosen using the electronic control unit based on the respective electrical characteristics of the plurality of electrodes. For instance, the ECU can measure the electrical coupling index or impedance among various electrodes and determine which of the respective electrodes are in contact with the tissue based on a threshold electrical coupling index or impedance value. In an example, determining select electrodes that are in contact with the tissue can include comparing the relative impedance between two or more electrodes and measuring the electrical signal from selected electrodes that are associated with an impedance value that is below a threshold impedance value. In a further example, the ECU can choose the select electrodes based on the measured strength of the electrophysiological signal detected at the respective electrodes. For instance, electrodes having greater signal strength as compared to a signal strength of other electrodes can be determined to be in contact with the tissue. In an example, an electrode located in the blood pool can detect different electrical characteristics of the electrophysiological signal than electrodes in contact with the tissue. Electrodes having a signal strength that exceeds a threshold strength value can be selected for measuring the electrophysiological signal. In some examples, contact force with the tissue can be measured using the electrical characteristic of the select electrodes. In another example, determining which electrodes are in contact with the tissue can include determining if two or more electrical contacts are electrically shorted to one another. Electrodes that are shorted to one another can be excluded from the select electrodes calculated to be in contact with the tissue. In yet further examples, select electrodes can be chosen using a combination of the examples discussed herein.

At 708, the location of the electrodes, such as the one or more select electrodes in contact with the tissue, can be calculated using the electronic control unit. In an example, the location (e.g., location 308, 408, or 508 as shown and described herein) of the electrodes can be calculated by the ECU. For instance, the location of the electrodes can be calculated with respect to a datum (e.g., coordinate system of the mapping balloon, such as datum 320). In some examples, the location of the electrodes can be calculated based on various factors. In various examples, the factors can include the size and shape of the various outer facing portions and inner fold portions, the location of the electrode along the respective outer facing portion or inner fold portion, the configuration of the mapping balloon (e.g., the collapsed, intermediate, or expanded configuration), or any combination thereof.

In an example, the location of the electrodes, such as the select electrodes, can be calculated based on an inflation pressure of the mapping balloon. For instance, the inflation pressure can be calibrated to correspond with a known dimension of the balloon, configuration state of the balloon, or to a known location of one or more of the electrodes. In another example, the configuration of the balloon can be adjusted with a mechanical linkage. The position of the mechanical linkage can be calibrated to the geometry of the balloon at a particular configuration state. The locations of the various electrodes can be calculated based on the known geometry of the balloon at the particular configuration state.

In a further example, the electric-field-based positioning system 136 or the magnetic-field-based positioning system 138 can be used to detect the location of one or more of the electrodes (e.g., the locational electrodes 134 or one or more electrodes 304). The locations of other electrodes can be calculated by the ECU based on the detected location of the electrodes from the electric-field-based positioning system 136 or the magnetic-field-based positioning system 138. For instance, the ECU can detect respective electrical characteristics of the various electrodes. The ECU can calculate the location of the plurality of electrodes based on the respective electrical characteristics. For instance, the ECU can calculate the location of the various electrodes based on a computed impedance value for the respective electrodes. Where an electric-field-based position system 136 is used, the respective impedance values can be used to determine the location of the various electrodes with respect to patch electrodes, such as patch electrodes $144_{x1, y1, z1, x2, y2, z2}$ (as shown and described in FIG. 1).

In yet another example, an electrical characteristic (e.g., electrical coupling index) between two or more electrodes can be used to determine the locations of the plurality of electrodes. For instance, the electrical characteristic between electrodes can correspond to specific locations of the plurality of electrodes based on the known geometry of the balloon (e.g., the size and shape of the various outer facing portions and inner fold portions and the location of the electrode along the respective outer facing portion or inner fold portion). In a further example, the electrical characteristics between various electrodes can be used to detect the configuration state of the balloon. For instance, where the inner fold portions of the balloon are touching, an electrical short between electrodes located along the inner fold portions can be detected. Accordingly, the ECU can determine that the inner fold portions of the balloon are touching, and thus, the ECU can detect that the balloon is in the collapsed configuration. In another example, the predefined fold locations and positions of the electrodes along the exterior surface can be configured so the ECU can detect various configuration states of the balloon by detecting contact between specific pairs of electrodes that are arranged to contact one another in a particular configuration of the balloon.

At 710, a map can be generated of the one or more electrodes using the electronic control unit. The map can be presented on a display (e.g., the display 140 as shown in FIG. 1 and described herein) communicatively coupled to the ECU. In an example, the graphical user interface of the display can present the geometry measurements, electrophysiological signal measurements, or a combination thereof. For instance, the map can include a three-dimensional representation of the tissue and include indicia representative of respective electrophysiological signals detected using the electrodes. The graphical user interface can be updated, for example, in real-time to present geometric or electrophysiological signal measurements. In a further example, the map can present geometric or electrophysiological signal data from electrodes that are determined to be in contact with the tissue or electrodes that are determined not to be in contact with the tissue. In an example, the map can be generated to display results only from electrodes that are determined to be in contact with the tissue. For instance, measurements from electrodes that are determined not to be in contact with the tissue can be excluded from the map presented on the display.

Figure 8:
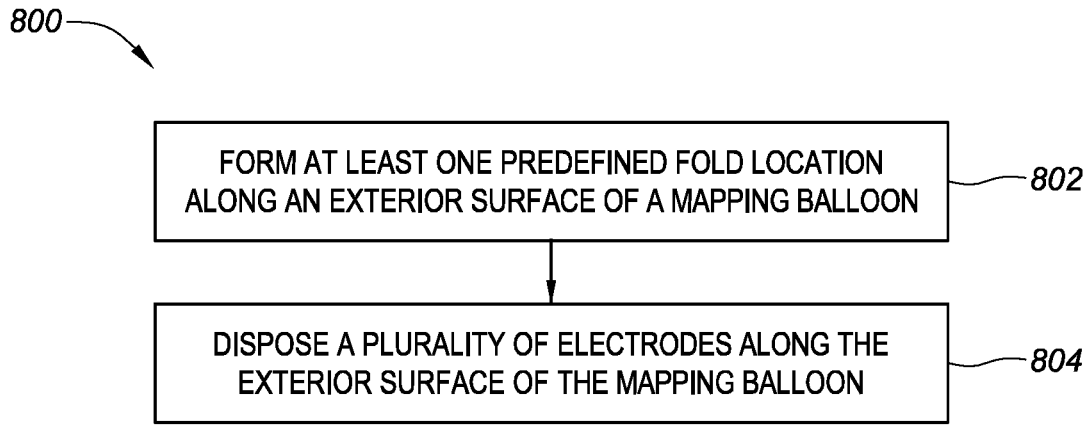
FIG. 8 is an example of a method of making a mapping balloon, according to an embodiment.

FIG. 8 is a method 800 of making a mapping balloon, such as the mapping balloons 158, 300, or 600A-F previously described in the examples herein and shown, for instance, in FIGS. 2-6. At 802, at least one predefined fold location, such as predefined fold location 306, can be formed along an exterior surface (e.g., exterior surface 302) of the mapping balloon. In various examples, the mapping balloon can be constructed of a material including, but not limited to, polyester, polyurethane, polyethylene, or the like. The predefined fold location can be configured to bend. Accordingly, the exterior surface of the mapping balloon can be adjusted between a collapsed configuration, an expanded configuration, or any configuration therebetween (e.g., the intermediate configuration). In an example, the mapping balloon can include a first dimension (e.g., dimension D1) in the collapsed configuration and a second dimension (e.g., dimension D3) in the expanded configuration, where the second dimension is greater than the first dimension. In an example, the predefined fold locations can be thermo-set into the material of the exterior surface of the mapping balloon. For instance, the exterior surface of the mapping balloon can be heated and shaped by a mold to form the predefined fold location. In an example, the mapping balloon, including the predefined fold locations can be blow molded. As previously described, the predefined fold locations can define an outer facing portion (e.g., outer facing portion 312) and an inner fold portion (e.g., 314). When the mapping balloon is in the intermediate or collapsed configurations, at least a portion of the inner fold portion is located closer to a longitudinal axis of the mapping balloon than the outer facing portion. In a further example, the forming the predefined fold location can include thinning the cross section of the exterior surface to create the predefined fold location. For example, the exterior surface of the mapping balloon can include a plurality of layers. The number, thickness, or bending modulus of the plurality of layers can be decreased (thinned) along the predefined fold locations. In a further example, the material of the exterior surface can be thinned to construct the predefined fold location. For instance, material can be removed from the exterior surface or the thinned section can be molded into the exterior surface to generate the predefined fold locations.

In an example, one or more predefined fold locations can be arranged along the exterior surface to define a first external shape in the collapsed configuration and a second external shape in the expanded configuration. For instance, the external shape can include, but is not limited to, a spherical (as shown in the example of FIG. 3), semi-spherical, ovoid shape, or other shape. In the collapsed configuration, the inner fold portions can be folded together and the outer facing portions can define the external shape of the mapping balloon. For instance, in the collapsed configuration, the predefined fold locations on the perimeter of one of the outer facing portions can be located adjacent to, or touching, predefined fold locations along adjacently located outer facing portions. The predefined fold locations can be arranged so the movement and relative positions of the various outer facing portions and inner fold portions can follow a repeatable pattern as the mapping balloon is adjusted between the collapsed configuration and the expanded configuration. Accordingly, the position and shape of the outer facing portions and inner fold portions can be consistent in the collapsed configuration, expanded configuration, or at any configuration therebetween, such as the intermediate configuration. For example, the exterior surface of the mapping balloon can fold in a predictable manner based on the predefined fold locations. In the expanded configuration, the predefined fold locations can be arranged to unbend and align the outer facing portions and inner fold portions. For instance, the outer facing portions and inner fold portions can be configured to be aligned (e.g., tangent or nearly tangent) in a spherical, ovoid, prolate, or other arrangement to define the exterior shape of the mapping balloon. A dimension of the mapping balloon, such as an overall dimension D3, transverse to the longitudinal axis of the mapping balloon, can be larger than the corresponding dimension (e.g., D1 and D2) of the mapping balloon in other configurations, such as the collapsed configuration or the partially collapsed (intermediate) configuration.

At 804, a plurality of electrodes, such as electrodes 304, can be disposed along the exterior surface of the mapping balloon. In various examples, the electrodes can be disposed along the exterior surface using a process including, but not limited to, aerosol jet printing, screen printing, additive or subtractive metallization, or the like. In a further example, the electrodes can be disposed along a flexible or compliant substrate, and the substrate can be attached (e.g., bonded) to the exterior surface of the mapping balloon. In some instances, the electrodes or electrical conductors (e.g., traces) can be constructed of a compliant conductive material. For example, the compliant conductive material can be a conductive ink, composite material having a flexible substrate with conductive particles embedded therein, or a conductive material having a strain relief feature configured to increase the extensibility of the conductive material. In a further example, the plurality of electrodes can be electrically coupled to an ECU, such as the ECU 142. Accordingly, the plurality of electrodes can be configured to communicate an electrical signal with the ECU.

The plurality of electrodes can be disposed with clinically uniform spacing as measured along the exterior surface. In an example, the plurality of electrodes can be positioned to have clinically uniform spacing in the collapsed configuration, the expanded configuration, or any configuration therebetween. In some examples, the electrodes can be disposed between the predefined fold locations along the exterior surface. The position of the electrodes can be configured so the electrodes follow a predictable path as the mapping balloon is adjusted between the collapsed configuration and the expanded configuration. The predictable path of the electrodes can be based on the calculable and consistent movement of the exterior surface, in particular the outer facing portions and inner fold portions, as the balloon is adjusted between the collapsed configuration and the expanded configuration.

Although several embodiments have been described above with a certain degree of particularity, those skilled in the art could make numerous alterations to the disclosed embodiments without departing from the spirit of the present disclosure. It is intended that all matter contained in the above description or shown in the accompanying drawings shall be interpreted as illustrative only and not limiting. Changes in detail or structure can be made without departing from the present teachings. The foregoing description and following claims are intended to cover all such modifications and variations.

Various embodiments are described herein of various apparatuses, systems, and methods. Numerous specific details are set forth to provide a thorough understanding of the overall structure, function, manufacture, and use of the embodiments as described in the specification and illustrated in the accompanying drawings. It will be understood by those skilled in the art, however, that the embodiments can be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein can be representative and do not necessarily limit the scope of the embodiments, the scope of which is defined solely by the appended claims.

Reference throughout the specification to "various examples," "some examples," "one example," "an example," or the like, means that a particular feature, structure, or characteristic described in connection with the example is included in at least one embodiment. Thus, appearances of the phrases "in various examples," "in some examples," "in one example," "in an example," or the like, in places throughout the specification are not necessarily all referring to the same example. Furthermore, the particular features, structures, or characteristics can be combined in any suitable manner in one or more embodiments. Thus, the particular features, structures, or characteristics illustrated or described in connection with one embodiment can be combined, in whole or in part, with the features structures, or characteristics of one or more other embodiments without limitation.

It will be appreciated that the terms "proximal" and "distal" can be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" can be used herein with respect to the illustrated embodiments. However, surgical instruments can be used in many orientations and positions, and these terms are not intended to be limiting and absolute.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A catheter comprising:
a catheter shaft configured for navigation within a body;
a mapping balloon coupled to the catheter shaft, the mapping balloon having an exterior surface including a plurality of predefined fold locations configured to allow the mapping balloon to be adjusted between a collapsed configuration and an expanded configuration, the exterior surface having a plurality of outer facing portions and a plurality of inner fold portions, wherein, in the collapsed configuration, edges of adjacent outer facing portions of the plurality of outer facing portions contact each other to form a first circular exterior surface of the mapping balloon, wherein, in the expanded configuration, the plurality of outer facing portions and the plurality of inner fold portions form a second circular exterior surface having a larger diameter than the first circular exterior surface; and
a plurality of electrodes located along the exterior surface to communicate electrical signals with an electronic control unit.

2. The catheter of claim 1, wherein the predefined fold locations are thermo-set fold locations.

3. The catheter of claim 1, wherein the mapping balloon includes an intermediate configuration between the collapsed configuration and the expanded configuration, and in the collapsed configuration and the intermediate configuration,
wherein the plurality of outer facing portions and the plurality of inner fold portions are defined by the predefined fold locations, wherein at least a portion of each of the plurality of inner fold portions is located closer to a longitudinal axis of the mapping balloon than the plurality of outer facing portions.

4. The catheter of claim 3, wherein the plurality of electrodes include primary electrodes and secondary electrodes, the primary electrodes located on the plurality of outer facing portions and the secondary electrodes located on the plurality of inner fold portions.

5. The catheter of claim 4, wherein the primary electrodes are configured to make first contact with tissue as the mapping balloon is adjusted from the collapsed configuration toward the expanded configuration.

6. The catheter of claim 4, wherein the spacing between the primary electrodes is clinically uniform along at least one of the outer facing portions or at least one of the inner fold portions when the mapping balloon is in the collapsed configuration or the expanded configuration.

7. The catheter of claim 1, wherein locations of the plurality of electrodes are configured to follow a predictable path between the collapsed configuration and the expanded configuration.

8. The catheter of claim 1, wherein the predefined fold locations are living hinges within the exterior surface.

9. The catheter of claim 1, wherein the plurality of predefined fold locations are configured for bending in a predictable manner between the collapsed configuration and the expanded configuration.

10. A system for operating a catheter, the system comprising:
- an input device configured for communication with a mapping balloon, wherein the mapping balloon includes an exterior surface having a plurality of electrodes located thereon, and the mapping balloon includes predictable shapes in various configurations including at least in a collapsed configuration and an expanded configuration, the input device further adapted to receive a position of a datum of the mapping balloon using a positioning system;
- a memory configured to store predictable shapes of the mapping balloon at the various configurations; and
- a processor configured for communication with the memory and the input device, the processor adapted to:
  - identify a geometry of the balloon corresponding to one of the predictable shapes stored in memory based on a detected configuration of the mapping balloon,
  - calculate respective locations of the plurality of electrodes based on the position of the datum and the identified geometry, and
  - choose select electrodes of the plurality of electrodes for measurement of geometry or electrophysiological signals corresponding to tissue.

11. The system of claim 10, wherein the mapping balloon includes a plurality of predefined fold locations along the exterior surface, the predefined fold locations are configured to bend to adjust the mapping balloon between the collapsed configuration and the expanded configuration, and wherein the mapping balloon includes at least one outer facing portion and at least one inner fold portion, the at least one outer facing portion and the at least one inner fold portion are defined by the predefined fold locations and move in a predictable manner between the collapsed configuration and the expanded configuration.

12. The system of claim 11, wherein the processor is configured to choose the select electrodes that are respective electrodes located along the at least one outer facing portion.

13. The system of claim 10, wherein the input device is further adapted to detect an electrical characteristic at the respective electrodes, and the processor is adapted to choose the select electrodes based on the electrical characteristic detected at the respective electrodes.

14. The system of claim 13, wherein the electrical characteristic is an electrical coupling index between at least two of the plurality of electrodes.

15. The system of claim 10, wherein the processor is further configured to calculate respective locations of the plurality of electrodes based on detecting a location of one or more locational electrodes using the positioning system, the one or more locational electrodes located along the exterior surface.

16. The system of claim 13, wherein the processor is further configured to construct a geometric model of the tissue based on the respective locations and the respective electrical characteristics of the plurality of electrodes and map the electrophysiological signals for presentation on a display.

17. A method for making a mapping balloon, the method comprising:
- forming at least one predefined fold location along an exterior surface of the mapping balloon, the predefined fold location configured to bend the exterior surface of the mapping balloon between a collapsed configuration and an expanded configuration, the exterior surface having a plurality of outer facing portions and a plurality of inner fold portions,
- wherein the mapping balloon includes a first dimension of an outer perimeter of the mapping balloon in the collapsed configuration and a second dimension of the outer perimeter of the mapping balloon in the expanded configuration, the second dimension greater than the first dimension,
- wherein, in the collapsed configuration, edges of adjacent outer facing portions of the plurality of outer facing portions contact each other to form the first dimension of the outer perimeter of the mapping balloon,
- wherein, in the expanded configuration, the plurality of outer facing portions and the plurality of inner fold portions form the second dimension of the outer perimeter of the mapping balloon; and
- disposing a plurality of electrodes along the exterior surface of the mapping balloon, each of the plurality of electrodes configured to communicate an electrical signal with an electronic control unit.

18. The method of claim 17, wherein the predefined fold locations are thermo-set into the exterior surface of the mapping balloon.

19. The method of claim 17, wherein forming the at least one predefined fold location includes forming a thinned cross section in exterior surface.

20. The method of claim 17, wherein configuring the electrodes to communicate an electrical signal to the electronic control unit includes electrically coupling a compliant circuit to one or more of the electrodes.

* * * * *